US011254907B2

(12) United States Patent
Dardick et al.

(10) Patent No.: US 11,254,907 B2
(45) Date of Patent: Feb. 22, 2022

(54) FUNGAL VOLATILE ORGANIC COMPOUND ENHANCES PLANT S GROWTH CHARACTERISTICS

(71) Applicant: The United States of America as represented by the Secretary of Agriculture, Washington, DC (US)

(72) Inventors: Christopher D. Dardick, Shenandoah Junction, WV (US); Wojciech J. Janisiewicz, Frederick, MD (US); Zongrang Liu, Winchester, VA (US); Zhijian Li, Martinsburg, WV (US); Ann M Callahan, Sheperdstown, WV (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 16/357,452

(22) Filed: Mar. 19, 2019

(65) Prior Publication Data

US 2020/0045980 A1    Feb. 13, 2020

Related U.S. Application Data

(60) Provisional application No. 62/715,941, filed on Aug. 8, 2018, provisional application No. 62/645,360, filed on Mar. 20, 2018.

(51) Int. Cl.
| | | |
|---|---|---|
| *A01N 63/00* | (2020.01) | |
| *C12N 1/14* | (2006.01) | |
| *A01N 63/30* | (2020.01) | |
| *A01G 9/02* | (2018.01) | |
| *A01N 27/00* | (2006.01) | |
| *C12P 5/00* | (2006.01) | |
| *C12R 1/645* | (2006.01) | |

(52) U.S. Cl.
CPC ............... *C12N 1/145* (2021.05); *A01G 9/02* (2013.01); *A01N 27/00* (2013.01); *A01N 63/30* (2020.01); *C12N 1/14* (2013.01); *C12P 5/002* (2013.01); *C12R 2001/645* (2021.05)

(58) Field of Classification Search
CPC .......... A01N 63/30; A01N 27/00; A01G 9/02; C12N 1/14; C12N 1/145; C12P 5/002
See application file for complete search history.

(56) References Cited

U.S. PATENT DOCUMENTS

2016/0143295 A1* 5/2016 Hirsch .................... C12R 1/125
                                                            504/117

OTHER PUBLICATIONS

Menetrez et al. Indoor Built Environ. 2002; 11:208-213. (Year: 2002).*
Fincheira et al. Microbiological Research. 2018; 208: 63-75. (Year: 2018).*

* cited by examiner

*Primary Examiner* — David Browe
(74) *Attorney, Agent, or Firm* — John D. Fado; Maria Restrepo-Hartwig

(57) ABSTRACT

A method of increasing east one growth characteristic of a plant comprising growing a *Cladosporium sphaerospermum* strain in or on a medium in a container, where a headspace of said *C. sphaerospermum* in said container is in fluid communication with a headspace of said plant, where said *C. sphaerospermum* produces at least one volatile organic compound (VOC), where said at least one VOC produced by said *C. sphaerospermum* causes the plant to have an increase in at least one growth characteristic when compared to the growth characteristic of a plant which has not been exposed to the VOC, and where said *C. sphaerospermum* comprises an ITS1/2 consensus amplicon of SEQ ID NO: 5 and an ITS3/4 consensus amplicon of SEQ ID NO: 6.

Figure 1:

9 Claims, 27 Drawing Sheets
(14 of 27 Drawing Sheet(s) Filed in Color)
Specification includes a Sequence Listing.

FUNGAL VOLATILE ORGANIC COMPOUND ENHANCES PLANT S GROWTH CHARACTERISTICS

REFERENCE TO RELATED APPLICATIONS

This application claims the benefit of U.S. Provisional Applications No. 62/715,941, filed Aug. 8, 2018, which is incorporated herein by reference in its entirety.

BACKGROUND

This invention relates to the use of one or more volatile organic compounds produced by *Cladosporium sphaerospermum* to increase at least one growth characteristic in a plant after exposure of the plant to the volatile organic compound(s) (VOCs).

In recent years, the use of beneficial microbes to promote plant growth and improve nutrient availability has been widely exploited. Consequently, such efforts resulted in the development and release of a number of plant promoting microbial/biostimulant products marketed as biofertilizers, plant strengtheners, and phytostimulators. These products have been successfully applied to many staple crops, vegetables and ornamentals with positive responses from growers. In fact, the market demand for such products is increasing at a steady rate of 10% annually (Berg, G., *Appl. Microbiol. Biotechnol.*, 84:11-18 (2009)). The economic values from agricultural productivity enhancement and the saved operational costs resulting from the use of such microbial products are substantial and cannot be overlooked.

Currently, the majority of plant growth promoting microbial products target the rhizosphere to improve root growth and/or increase nutrient availability for a wide range of crops. For instance, Monsanto offers three products under the namely BioAg® tradename that utilize three different fungal/bacterial species under the initiative banner of "Bringing New Solutions to Modern Agriculture" (see, monsantobioag.com). Among these products, JUMP-START® seed treatment utilizes *Penicillium bilaii* growing along a plant's roots to release phosphate that has been bound to minerals and soil particles, thereby increasing the amount of phosphate in the soil for uptake by the seedlings/plants, and TAGTEAM® utilizes *Penicillium bilaii* to release phosphate and beneficial rhizobia to form nodules to increase nitrogen fixation. QUICKROOTS® utilize *Trichoderma virens* and *Bacillus amyloliquefaciens* to release phosphate in the soil that is not readily available to the plant. According to Monsanto, in 9-year field trials, QUICKROOTS® for wheat delivered an average 2.8 Bu/A advantage as compared to controls (80.2 vs 77.4 Bu/A).

In addition, numerous symbiotic mycorrhizal products have been developed and widely utilized worldwide. U.S. Patent Application Publication 2016/0143295 (Hirsch and Kaplan) describes the utilization of a wide range of microbes in the form of endophytes to promote plant growth, similar to a previous report that utilizes a fungus as an endophyte (Hamayun, et al., *Mycologia* 102:989-995 (2009)). All of these products are either applied to the soil, used to inoculate seeds/plants, or applied as an endophyte that lives inside the target plant. In other words, the effecting organisms are released to the environment/habitat and have to come in contact with the host plant.

Similarly, the study of microbial volatile organic compounds (MVOCs) capable of promoting plant growth through air space without direct contact between the microorganisms and effected plants has gained a new-found momentum. In fact, finding new microbes that possess the ability to emit plant-promoting MVOCs and developing practical means of application in large scale agriculture practice settings constitute a major effort in the forefront of microbial-based biostimulant research (Turner and Meadows-Smith, *Acta Hort.* (ISHS), 1148:105-108 (2016)). Kanchiswamy, et al., recently reported that 400 out of 10,000 described microbial species produce MVOCs that may function in chemical communication within ecological communities or with plant hosts either positively or negatively (see Kanchiswamy, et al., *Trends in Plant Sci.* 20:206-211 (2015a)). Since the early 70's, some MVOC-producers have been shown to be capable of promoting plant growth and enhancing plant immunity (Kanchiswamy, et al. (2015a)). Yet, only in recent years have extensive studies been conducted to characterize MVOCs. The molecular mechanisms associated with MVOC-induced growth stimulation remain enigmatic. Over the years, concerted search efforts have yielded a dozen bacterial and fungal organisms that produce stimulatory MVOCs for plant growth (Kanchiswamy, et al., *Frontiers in Plant Sci.* 6: article 151 (2015b)). In the best cases reported thus far, small tobacco plants exposed to MVOCs produced by *Cladosporium cladosporioides* CL-1 were able to increase growth by 2- to 3-fold within a three-week co-cultivation time period (Paul and Park, *Sensors* 13:13969-13977 (2013)). The levels of plant growth promotion induced by current MVOC-emitting microorganisms remain miniscule.

Two strains of endophytic *Cladosporium sphaerospermum*, DK1-1 and MH-6, isolated from plant roots have been shown to produce active gibberellic acids (GAs) with marginal growth promotion effects using culture filtrates (56% increase in plant height). But no *C. sphaerospermum* (*C. sp*) strains have been demonstrated to be MVOC-producers (see Hamayun, et al. (2009)), much less producers of MVOCs which increase a plant's growth and yield.

Because of the problems discussed above concerning use of microorganisms in the soil or as endophytes, and because of the need to improve plant growth and productivity, a need exists for identifying microorganisms that produce and release VOCs (MVOCs) that can increase plant growth and/or yield.

All of the references cited herein, including U.S. patents and U.S. patent application Publications, are incorporated by reference in their entirety.

Mention of trade names or commercial products in this publication is solely for the purpose of providing specific information and does not imply recommendation or endorsement by the U.S. Department of Agriculture.

SUMMARY

It is an object of this invention to have a method of increasing at least one growth characteristic of a treated plant compared to the growth characteristic of an untreated plant by exposing an untreated plant to at least one volatile organic compound (VOC) produced by *Cladosporium sphaerospermum*. It is another object of this invention that the *C. sphaerospermum* may contain ITS1/2 consensus amplicon of SEQ ID NO: 5 and ITS3/4 consensus amplicon of SEQ ID NO: 6. It is another object of this invention that the *C. sphaerospermum* may have Accession No. NRRL 67603, NRRL 8131, or NRRL 67749. It is further object of this invention that the at least one VOC causes at least one growth characteristic in the treated plant to increase more than the same growth characteristic in an untreated plant with a similar age. It is a further object of this invention that the at least one VOC may be present in the plant's headspace. It is another object of this invention that the plant's roots may be exposed to the at least one VOC.

It is an object of this invention that the at least one growth characteristic can be growth rate, aerial biomass weight, plant height, number of branches, number of leaves, leaf size, leaf weight, leaf thickness, leaf expansion rate, petiole size, petiole diameter, petiole thickness, stem thickness, branch thickness, trunk thickness (caliper), stem length, branch length, trunk length, stem weight, branch weight, trunk weight, canopy/branching architecture, root biomass, root extension, root depth, root weight, root diameter, root robustness, root anchorage, root architecture, abiotic stress tolerance (cold, heat, salinity and/or drought), anthocyanin pigment production, anthocyanin pigment accumulation, plant oil quality and quantity, secondary metabolite accumulation, sensory and flavor compound production, content of phytopharmaceutical or phytochemical compounds, fiber hypertrophy and quality, quantity of chlorophyll, photosynthesis rate, photosynthesis efficiency, leaf senescence retardation rate, early and efficient fruit set, early fruit maturation, fruit yield, yield of vegetative parts, root and tubers, fruit/grain and/or seeds, size of fruit, grain and/or seeds, firmness of fruit, grain and/or seeds, weight of fruit, grain and/or seeds, starch content of vegetative parts, root and tuber, fruit, grain, and/or seeds, sugar content of fruit, grain and/or seeds, content of organic acids in fruit and seeds, early flowering (flowering precocity), harvest duration, and a combination thereof.

Figure 8:
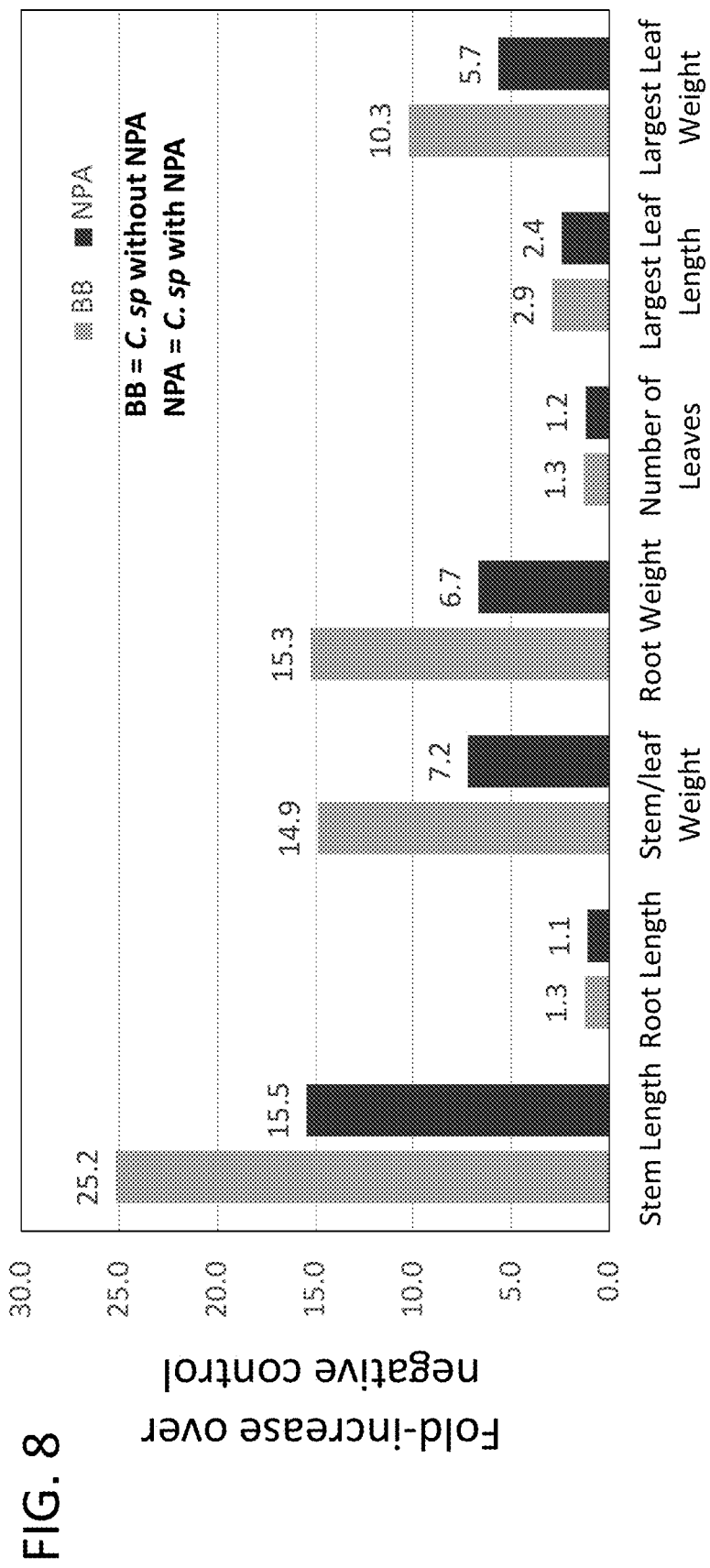

It is another object of this invention that the *C. sphaerospermum* may be grown in a container near the plant so that the at least one VOC can enter the plant's headspace. It is another object of this invention that the container in which the *C. sphaerospermum* is grown may be connected to an opening to the plant's headspace. It is another object of the invention that the container in which the *C. sphaerospermum* is grown may be within the container in which the plant is grown or within the plant's headspace. It is another object of this invention that the plant may be exposed to the at least one VOC for approximately 1 day. It is another object of this invention that the plant may be exposed to the at least one VOC for between approximately 1 day and approximately 20 days. It is a further object of this invention that the *C. sphaerospermum* may be grown in Murashige and Skoog medium, potato dextrose agar, Czapek-DOX Yeast agar, yeast extract agar, malt extract agar, or Hunter's medium.

It is a further object of the invention that the plant that is being treated can be a gymnosperm and angiosperm. It is further object of the invention that the plant being treated can be monocotyledon or dicotyledon. It is another object of this invention that the plant may be a seedling or seed. It is another object of this invention that the plant being treated may be older than approximately 1 year.

SEQUENCE LISTING

The Sequence Listing submitted via EFS-Web as ASCII compliant text file format (.txt) filed on Mar. 19, 2019, named "SequenceListing_ST25", (created on Mar. 20, 2018, 2 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BRIEF DESCRIPTION OF THE FIGURES

Advantages of embodiments of the present invention will be apparent from the following detailed description of the exemplary embodiments. The patent or application file contains at least one drawing executed in color. Copies of this patent or patent application publication with color drawing(s) will be provided by the office upon request and payment of the necessary fee. The following detailed description should be considered in conjunction with the accompanying figures in which:

Exemplary FIG. 1 shows the differences between six-day-old tobacco seedlings exposed to VOCs produced by *C. sphaerospermum* Accession No. NRRL 67603 for 10 days (left image) and negative control tobacco seedlings of same age that were not exposed to the VOCs (right image). "*C. sp*" represents *C. sphaerospermum* Accession No. NRRL 67603 contained in Eppendorf tubes plugged with filters.

Exemplary FIG. 2 shows the differences between six-day-old tobacco seedlings exposed to VOCs produced by *C. sphaerospermum* Accession No. NRRL 67603 for 20 days (bottom images) and negative control tobacco seedlings of same age that were not exposed to the VOCs (top images). "*C. sp*" represents *C. sphaerospermum* Accession No. NRRL 67603.

Exemplary FIG. 3 compares the roots, stem, and leaves of a six-day-old tobacco seedling exposed to VOCs produced by *C. sphaerospermum* Accession No. NRRL 67603 for 20 days (top plant) and a negative control tobacco seedling of same age that was not exposed to the VOCs (bottom plant).

Exemplary FIG. 4 compares the average stem length, shoot fresh weight, root fresh weight, and largest leaf weight of nine tobacco seedling (three seedlings per vessel) that were exposed to VOCs produced by *C. sphaerospermum* Accession No. NRRL 67603 for 20 days (grey) to nine negative control tobacco seedlings of same age (three seedlings per vessel) (black).

Exemplary FIG. 5 shows the "fold-increase" of stem length, root length, stem/leaf weight (defined as the combined weight of stem and all leaves; which also the weight of the entire above ground shoot with its leaves; can also be referred to "shoot biomass" or "aerial biomass"), root weight, number of leaves, largest leaf length and largest leaf weight of nine tobacco seedling (three seedlings per vessel) that were exposed to VOCs produced by *C. sphaerospermum* Accession No. NRRL 67603 for 20 days to nine negative control tobacco seedlings of same age (three seedlings per vessel).

Exemplary FIG. 6 shows the accelerated growth in 30-day old tobacco seedlings exposed to *C. sphaerospermum* Accession No. NRRL 67603 VOCs for seven days (right picture) compared to a 72-day old tobacco seedling that was not exposed to *C. sphaerospermum* Accession No. NRRL 67603 VOCs. The 72-day old negative control tobacco seedling has approximately 16 leaves while the 30-day old tobacco seedlings exposed to the MVOCs had approximately 10 leaves.

Exemplary FIG. 7 compares the effects of the indicated medium on which *C. sphaerospermum* Accession No. NRRL 67603 grows to its impact on the indicated tobacco plant growth characteristics. The average total plant height, number of leaves per plant, root length, total plant fresh weight, stem length, and largest leaf length are determined for one-month old tobacco plants exposed to *C. sphaerospermum* Accession No. NRRL 67603 VOCs for 20 days after seed sowing. "CK" is negative control (plant was not exposed to VOCs); "MS" is Murashige and Skoog medium; "PDA" is potato dextrose agar; "Czapek" is Czapek-DOX Yeast agar; "Malt" is malt extract agar; "Yeast" is yeast extract agar; and "Hunter's" is Hunter's medium.

Exemplary FIG. 8 illustrates the effect of 10 μM N-1-naphthylphihalamic naphthylphthalamic acid (NPA) on *C. sp* Accession No. NRRL 67603 VOCs impact on indicated growth characteristics of tobacco plants exposed to the VOCs for twenty days beginning when the plants were six days old compared to tobacco plants treated with only *C. sp* Accession No. NRRL 67603 VOCs for the same amount of time. The amounts of change are shown as fold-increase over the indicated measurements of negative control plants for growth characteristics of stem length, root length, stem/leaf weight, root weight, number of leaves, length of largest leaf, and weight of largest leaf. "BB" is *C. sp* treated plants without N-1-naphthylphthalamic acid. "NPA" is *C. sp* treated plants with 10 μM N-1-naphthylphthalamic acid.

Figure 9A:
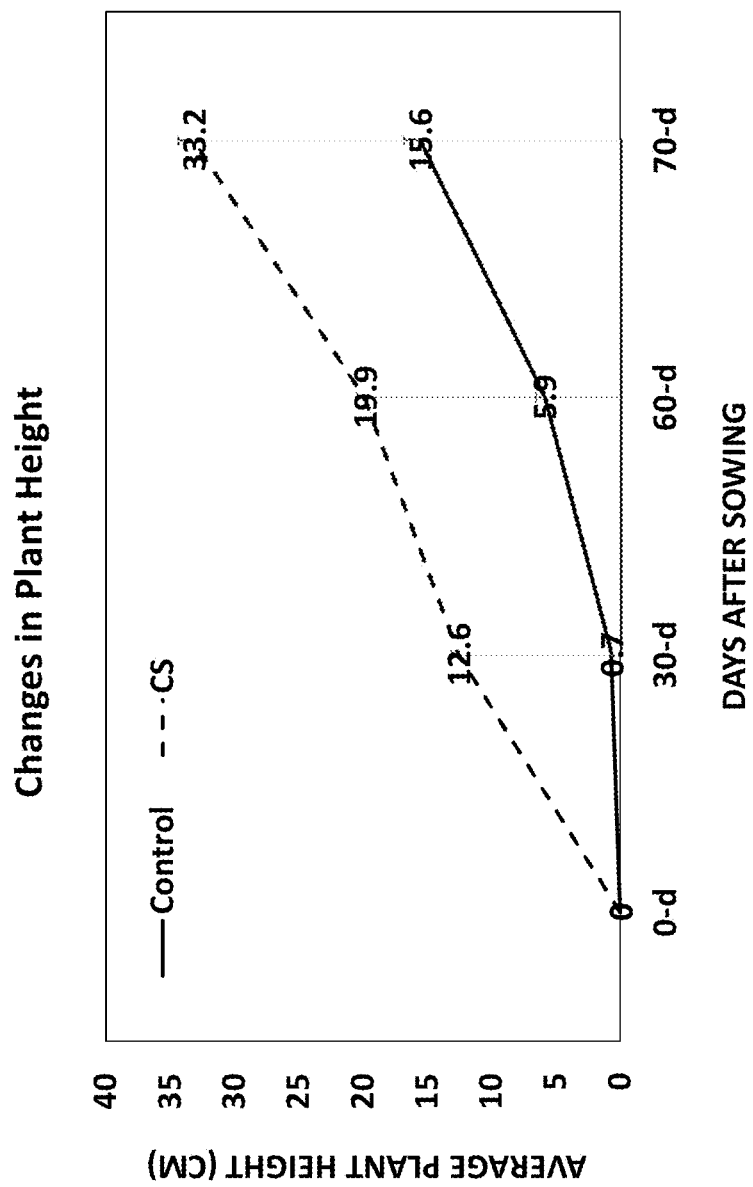
Figure 9B:
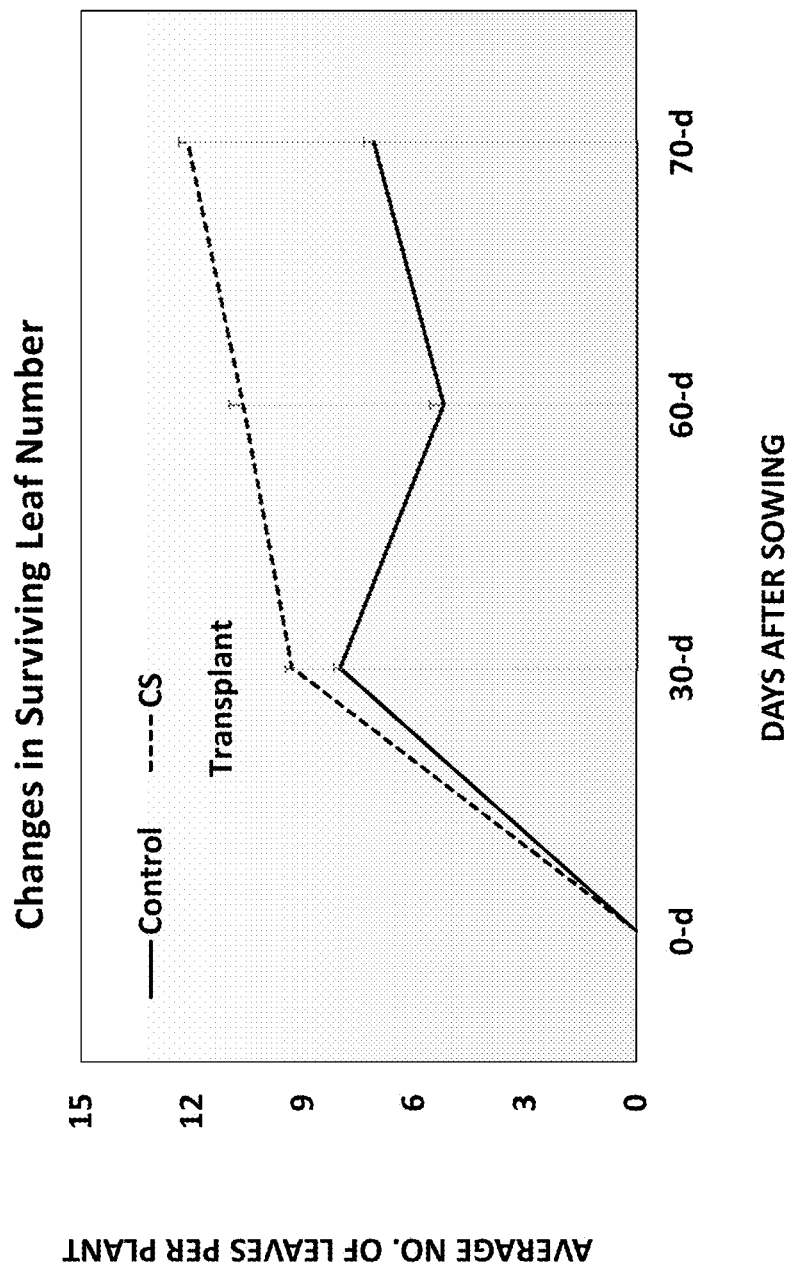
Figure 9C:
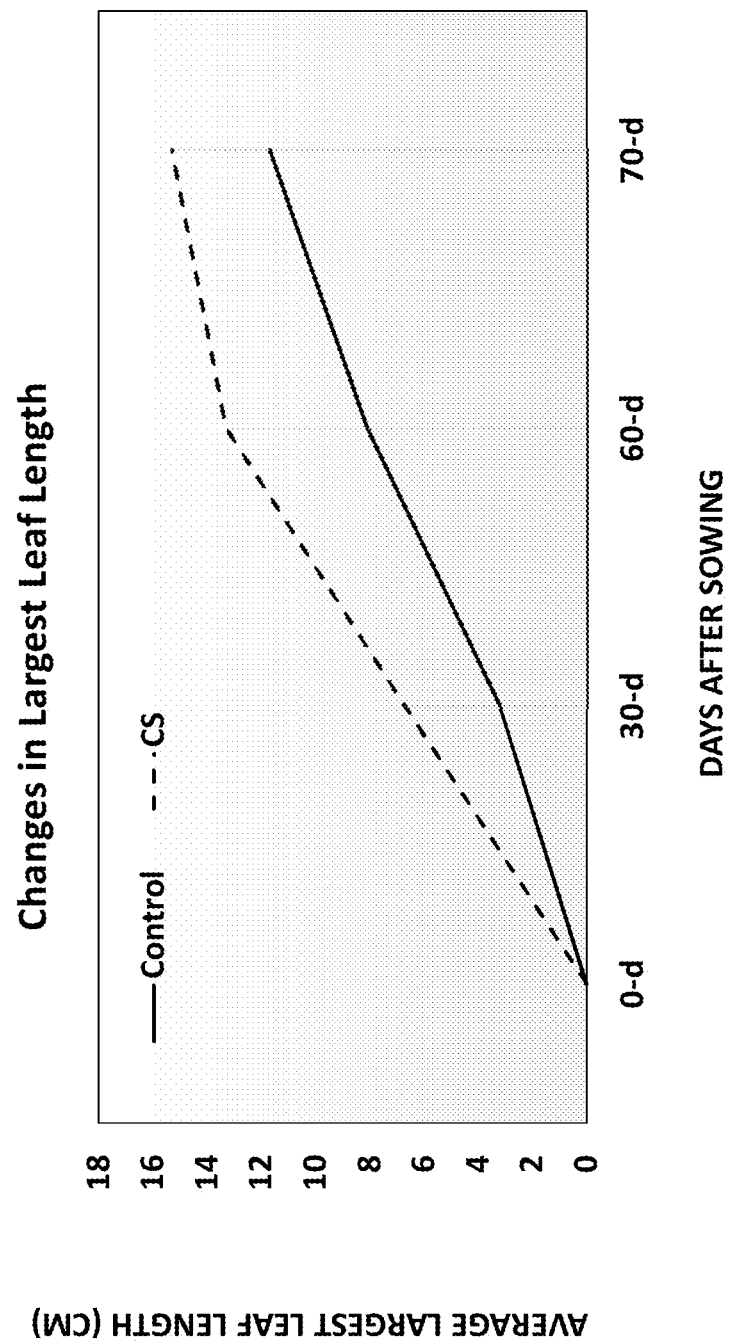

Exemplary FIG. 9A, FIG. 9B, and FIG. 9C show the long-term increase in the indicated tobacco plant growth characteristics after exposure to *C. sp* Accession No. NRRL 67603 VOCs. Six-day old tobacco seedlings are exposed to *C. sp* Accession No. NRRL 67603 VOCs for 20 days and then transplanted to soil. Average plant height (FIG. 9A), average number of leaves per plant (FIG. 9B), and average largest leaf length (FIG. 9C) are measured at 30 days, 60 days, and 70 days after germination. Measurements for negative control tobacco plants are indicated as a solid line; for *C. sp* Accession No. NRRL 67603 VOCs treated plants are indicated as a dashed line. For FIGS. 9A-9C, "control" means negative control plants; "CS" means plants exposed to *C. sp* Accession No. NRRL 67603 VOCs.

Figure 10:
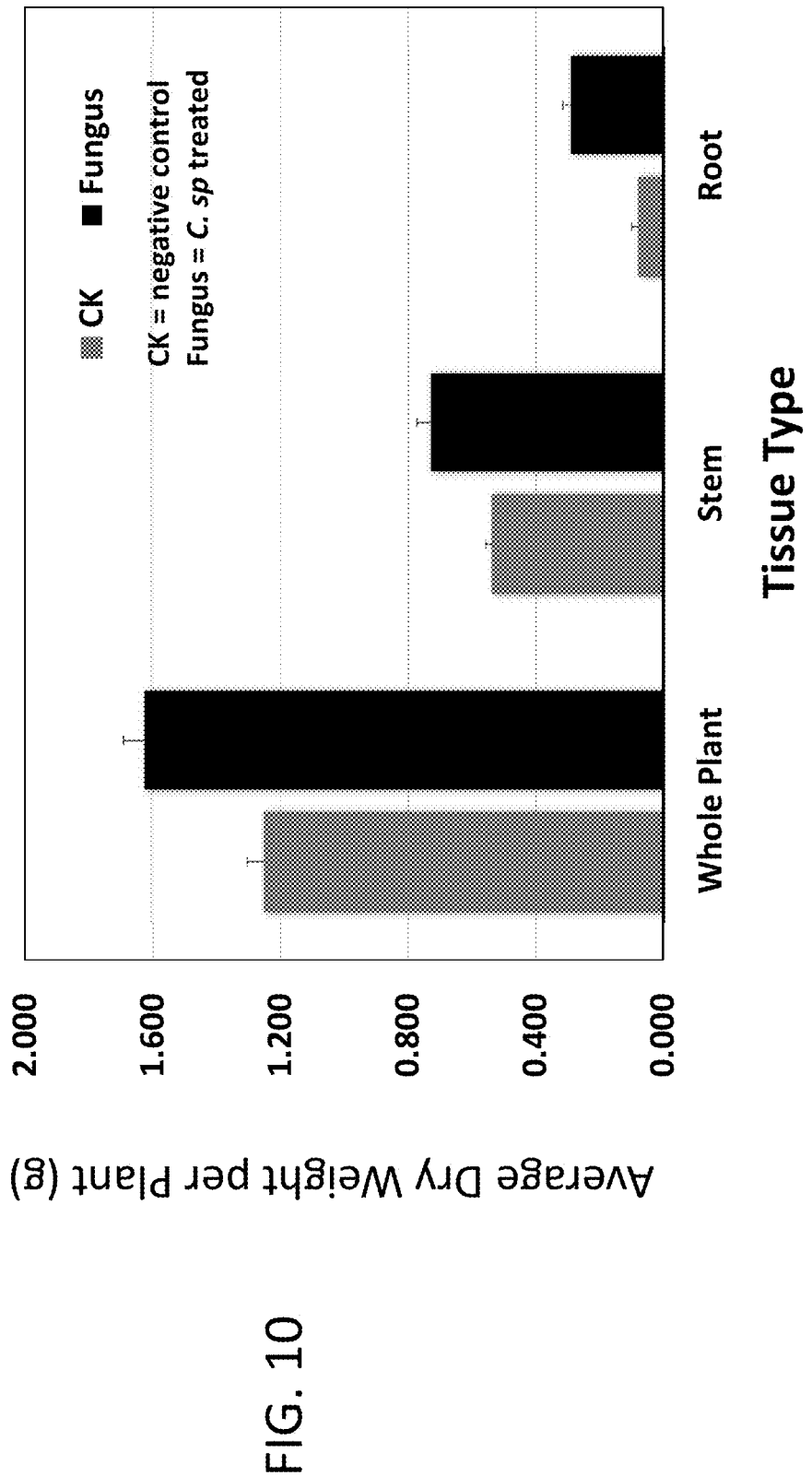

Exemplary FIG. 10 compares the average dry weight of the whole plant, stem tissue, or root tissue per tobacco plant either exposed to *C. sp* Accession No. NRRL 67603 VOCs or non-exposed (negative control). "CK" means negative control plants; and "*C. sp*" means tobacco plants exposed to *C. sp* Accession No. NRRL 67603 VOCs.

Figure 11:
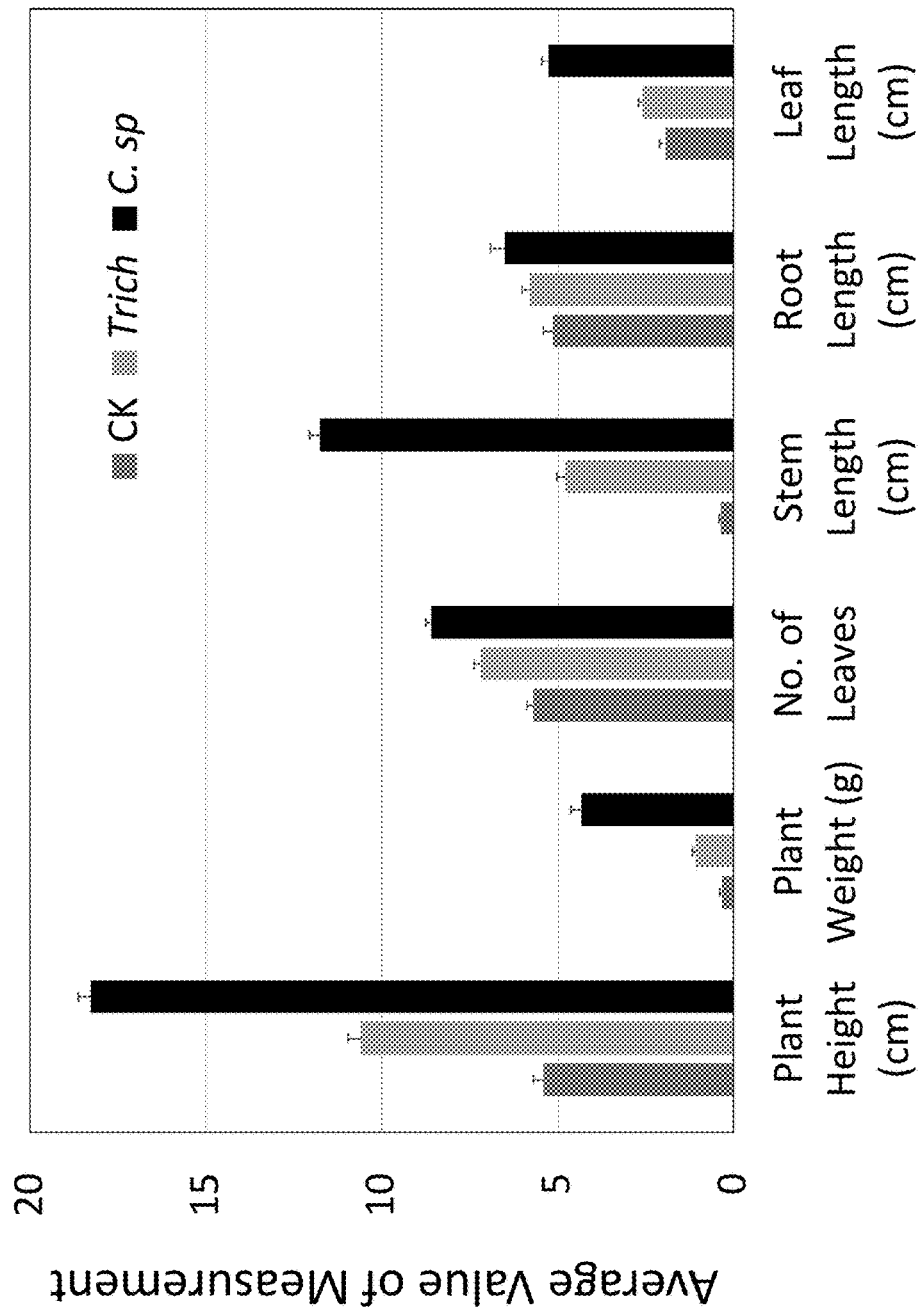

Exemplary FIG. 11 compares the various growth characteristics on tobacco plants from exposure to VOCs from *Trichoderma* or *C. sp* Accession No. NRRL 67603. Average plant height, weight, number of leaves, stem length, root length, and leaf length. "CK" means negative control plants; "Trich" means tobacco plants exposed to *Trichoderma* VOCs; and "*C. sp*" means tobacco plants exposed to *C. sp* Accession No. NRRL 67603 VOCs.

Figure 12:
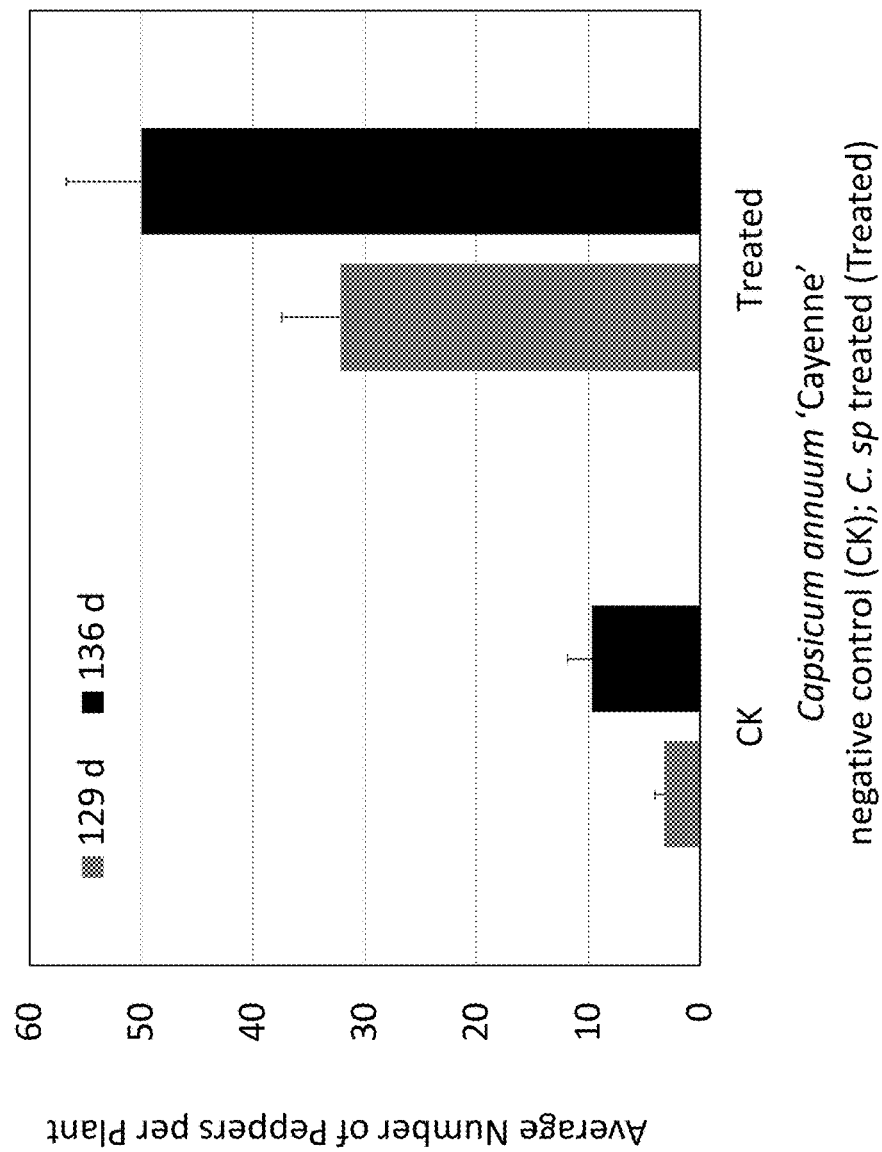

Exemplary FIG. 12 shows the difference in average number of cayenne peppers produced by a pepper plant (*Capsicum annuum* 'Cayenne') at 129 days and 136 days post-germination. "CK" means negative control plants; "Treated" means pepper plants exposed to *C. sp* Accession No. NRRL 67603 VOCs.

Figure 13A:
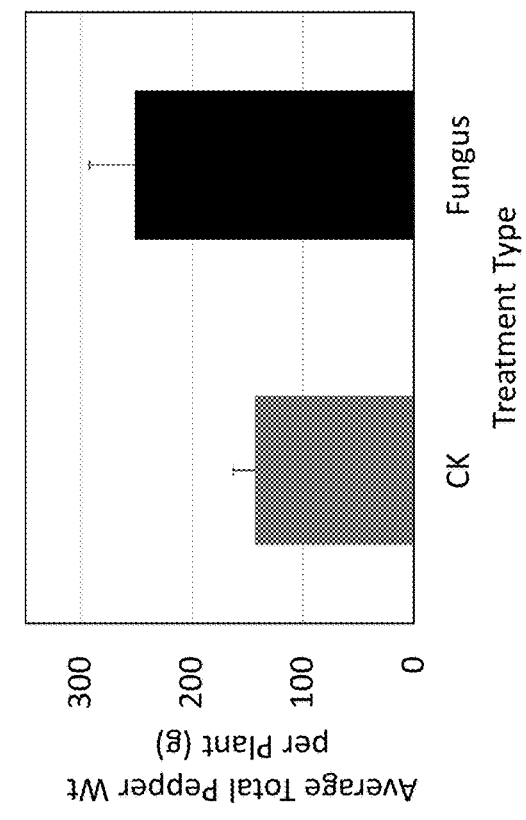
Figure 13B:
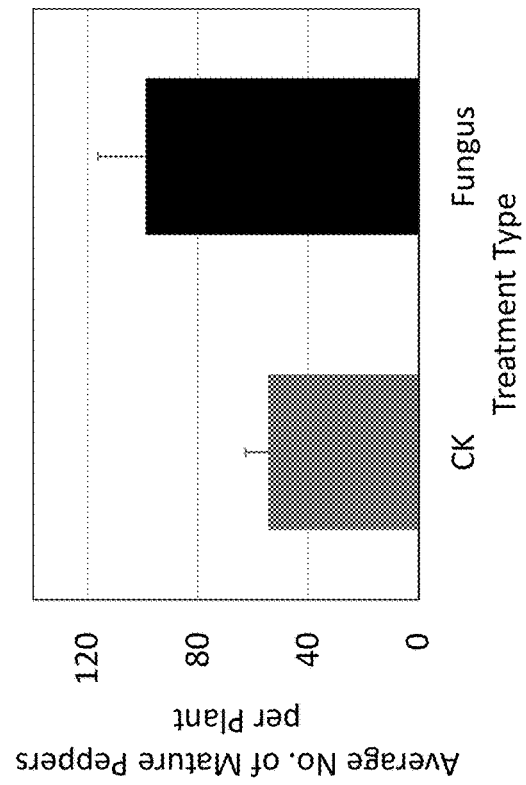

Exemplary FIG. 13A shows the average number of mature peppers per pepper plant (treated and untreated) at 157 days post-germination. Exemplary FIG. 13B shows the average total pepper weight per pepper plant (treated and untreated) at 157 days post-germination. "CK" is negative control (untreated) pepper plants. "Fungus" is pepper plant exposed to *C. sp* Accession No. NRRL 67603 VOCs (treated).

Figure 14:
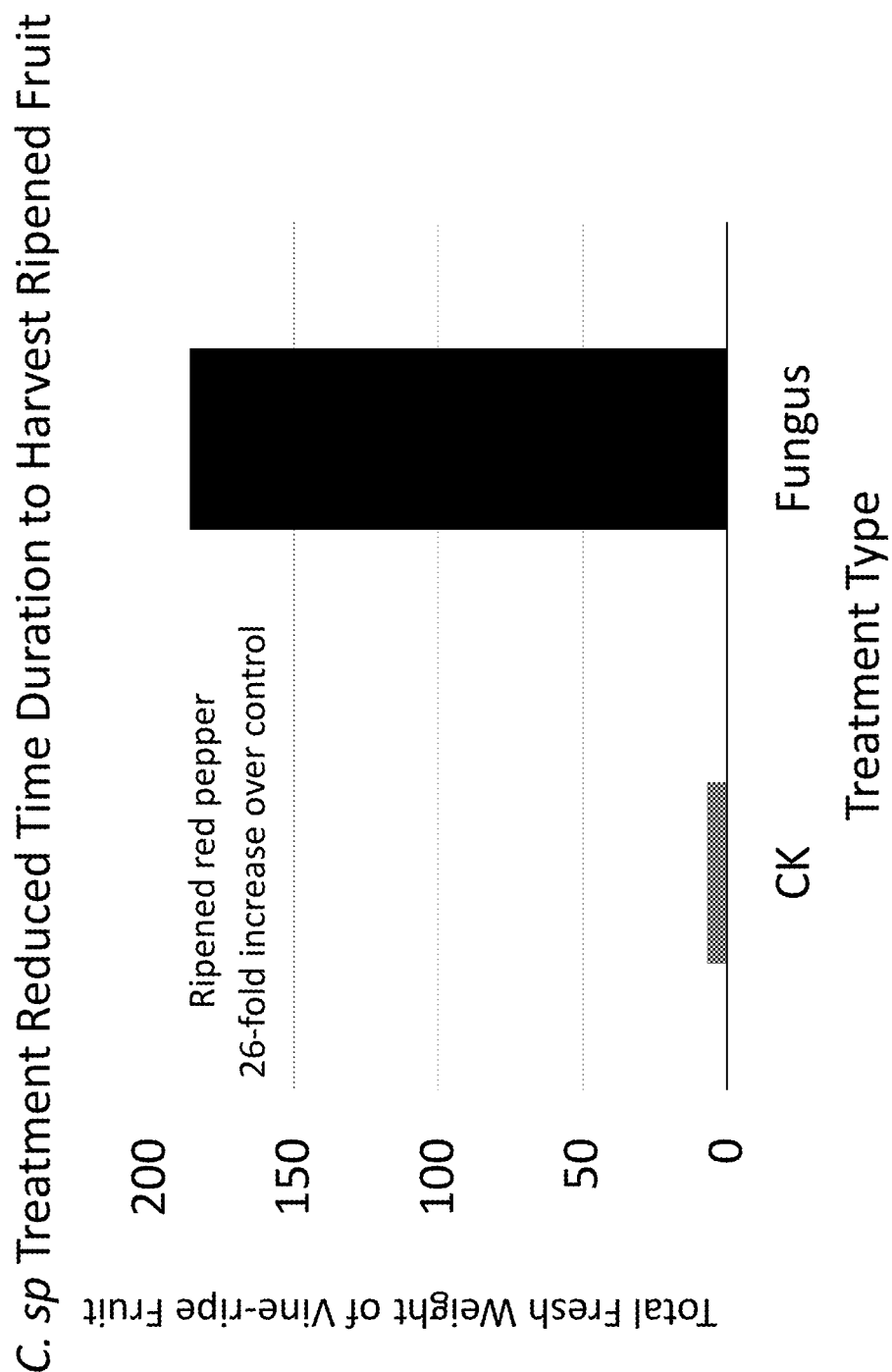

Exemplary FIG. 14 shows that pepper plants treated with *C. sp* Accession No. NRRL 67603 VOCs have shorter time to harvest (i.e., more vine-ripe (reddish in color) fruit) compared to untreated pepper plants as determined by the total fresh weight of vine-ripe peppers at 157 days post-sowing on negative control plants ("CK") versus *C. sp* Accession No. NRRL 67603 VOCs treated pepper plants ("Fungus").

Figure 15:
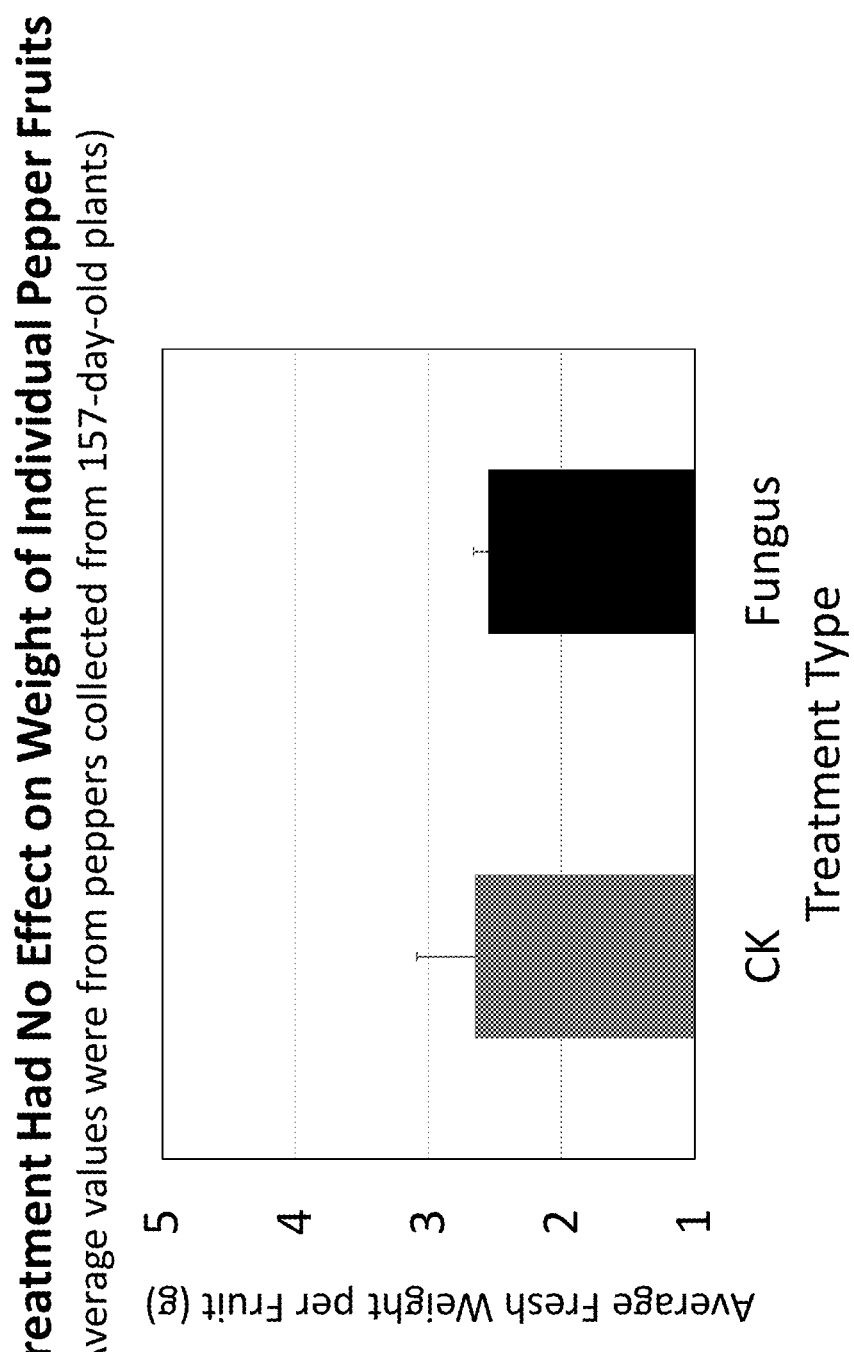

Exemplary FIG. 15 demonstrates that pepper plants exposed to *C. sp* Accession No. NRRL 67603 VOCs ("Fungus") does not increase the weight of individual peppers compared to the weight of individual peppers from negative control pepper plants ("CK").

Figure 16:

Exemplary FIG. 16 demonstrates improvement of root growth via exposure of in vitro shoots with root primordia to *C. sp* Accession No. NRRL 67603. In vitro shoots of 'Bailey-OP' were induced to form root primordia and then transferred to growth regulator-free medium without (Control) or with (TC09) exposure for 10 days. Bar at right top corner represents 1 cm.

Figure 17:
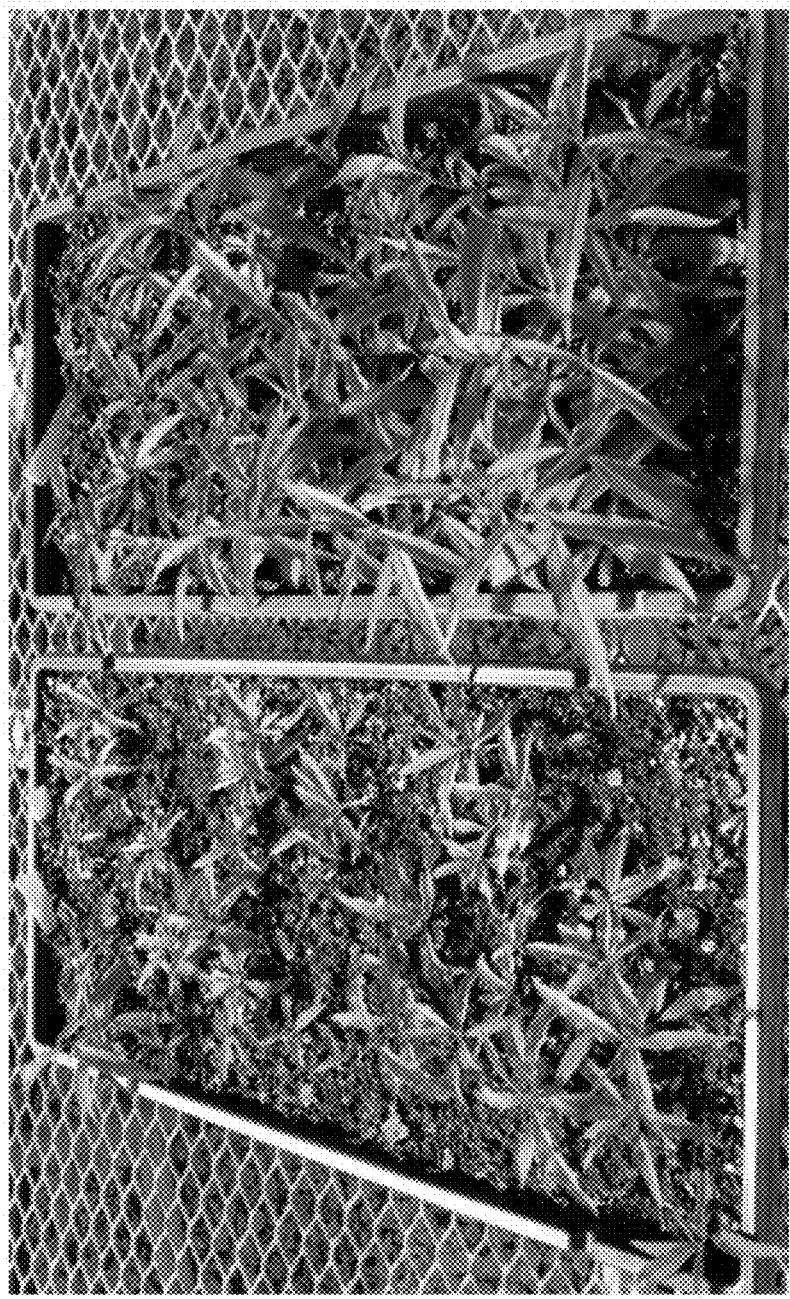

Exemplary FIG. 17 shows acclimatization of in vitro propagated plants of peach rootstock 'Bailey-OP' with and without exposure to *C. sp* Accession No. NRRL 67603. Rooted in vitro shoots were treated without (Control) or with (TC09) exposure to TC09 for 10 days and then transplanted to soil and maintained in the greenhouse for one month. In this representative comparison, control tray on left side contains 36 surviving plants out of 100 transplanted plants. Tray on right side contains plants with exposure to TC09 for 10 days prior to transplanting and has 46 surviving plants out of 52 transplanted plants.

Figure 18:
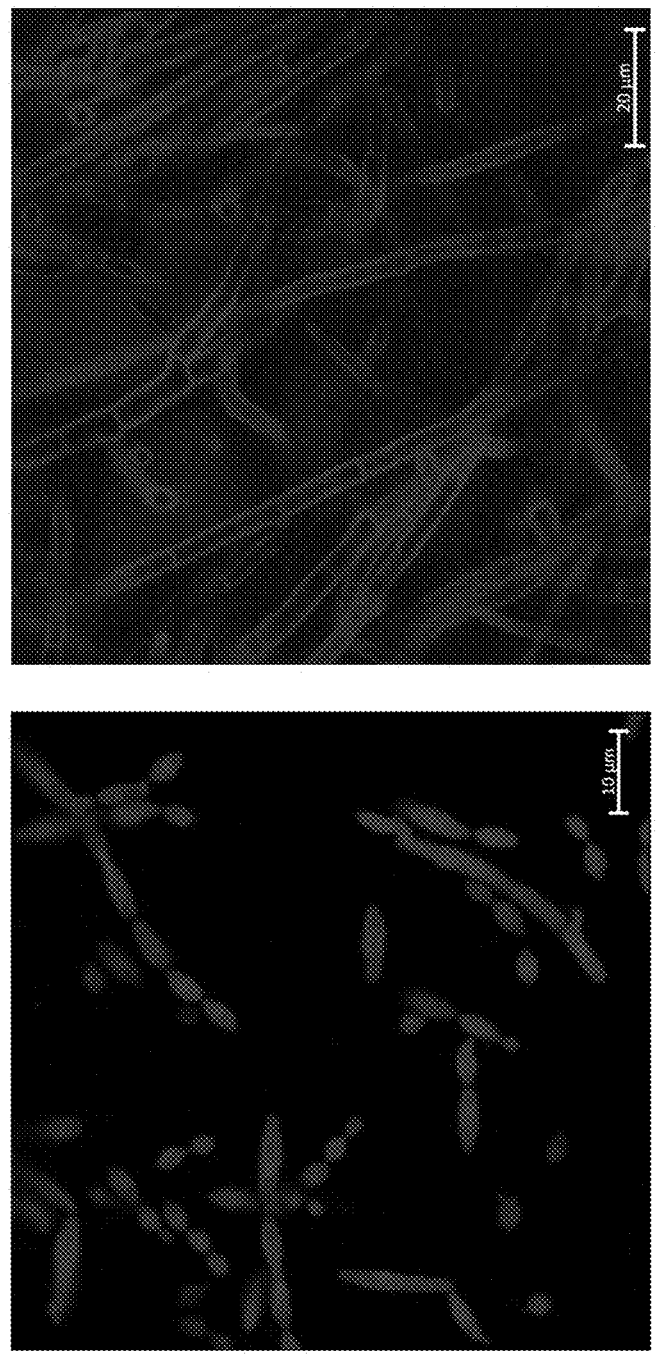

Exemplary FIG. 18 illustrates microscopic characterization of MK19, formation of conidia in chains with larger intercalary conidia and smaller terminal conidia (left); and mycelium septation and branching (right).

Figure 19:
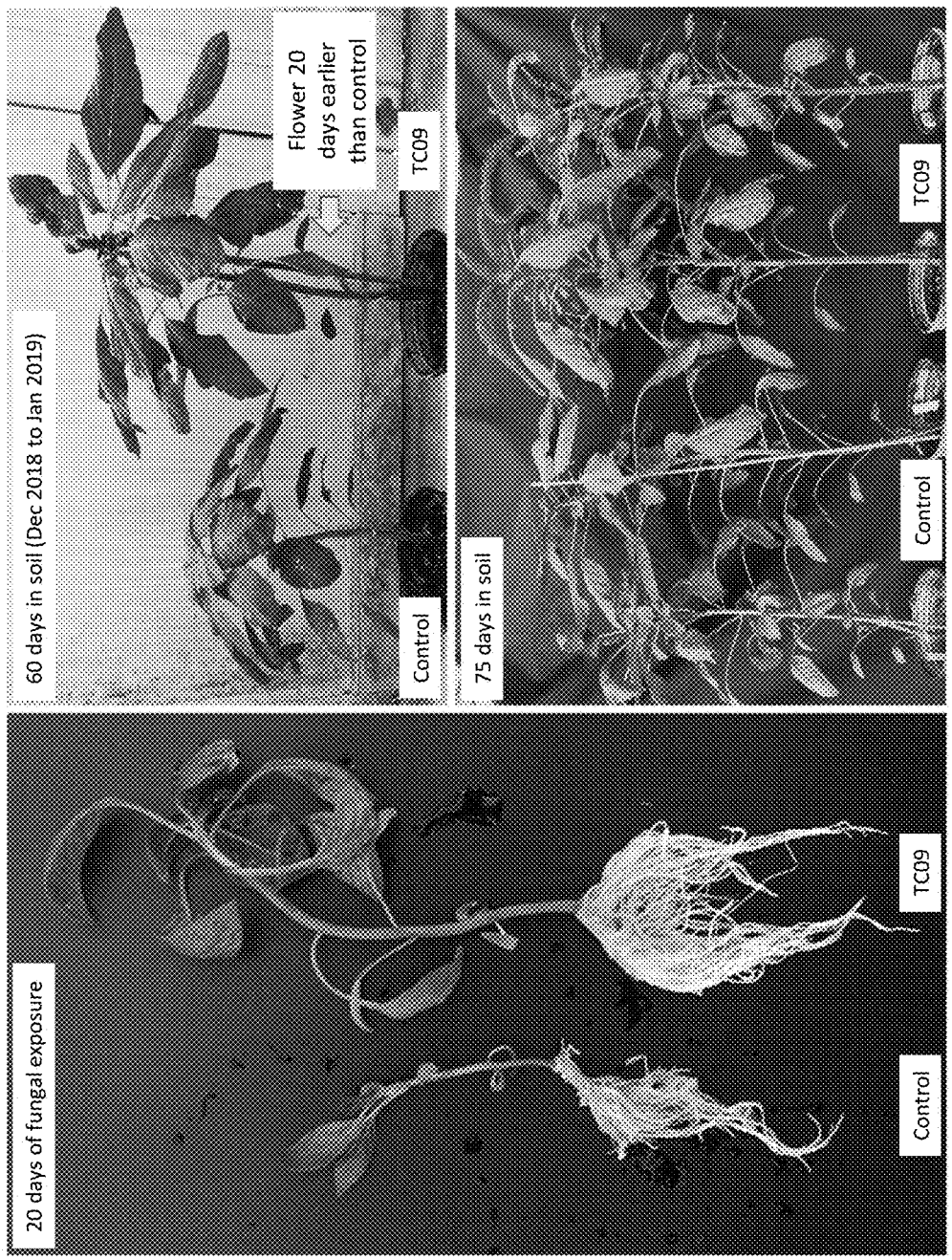

Exemplary FIG. 19 demonstrates plant growth promotion in Family Amaranthaceae, species *Amaranthus tricolor* at different stages of development as a result of exposure in vitro to *C. sp* VOCs. Control denotes negative control plants that were subject to identical tissue culture growth but without VOC exposure. The left panel shows one-month-old in vitro plants after sowing without (left, control) and with (right, treated) exposure to the fungus for 20 days. The right panels show plants at 60- and 75-days post transplanting.

Figure 20:
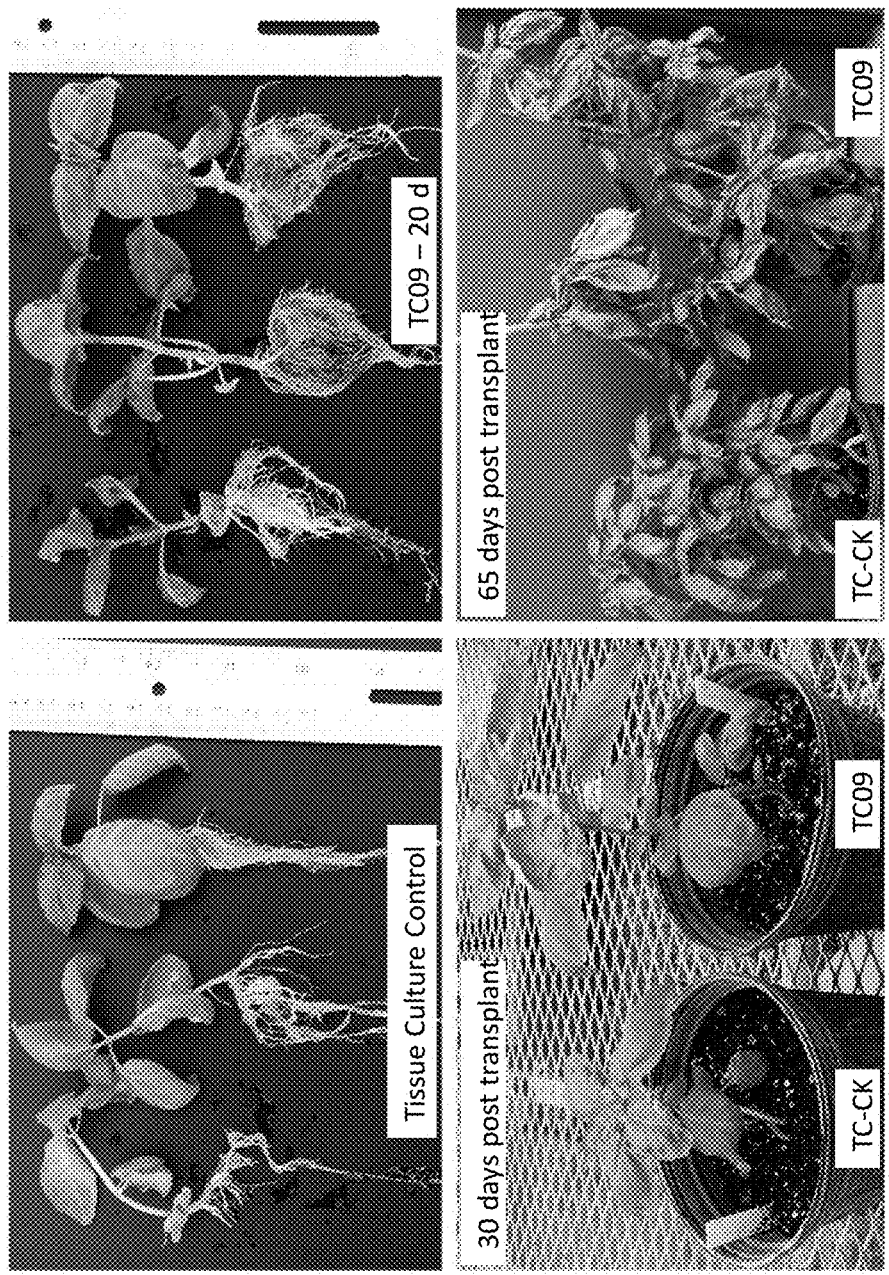

Exemplary FIG. 20 shows plant growth promotion in basil (Family Lamiaceae, species *Ocimum basilicum*) triggered by exposure in vitro to *C. sp* VOCs. Top pair images compare plant development at the end of one-month in vitro growth between control (left image) and treated plants (right image). The latter developed a massive robust root system. Bottom pair images illustrates plant size difference between these two treatments at 30 days (left image) and 65 days (right image) post transplanting.

Figure 21:
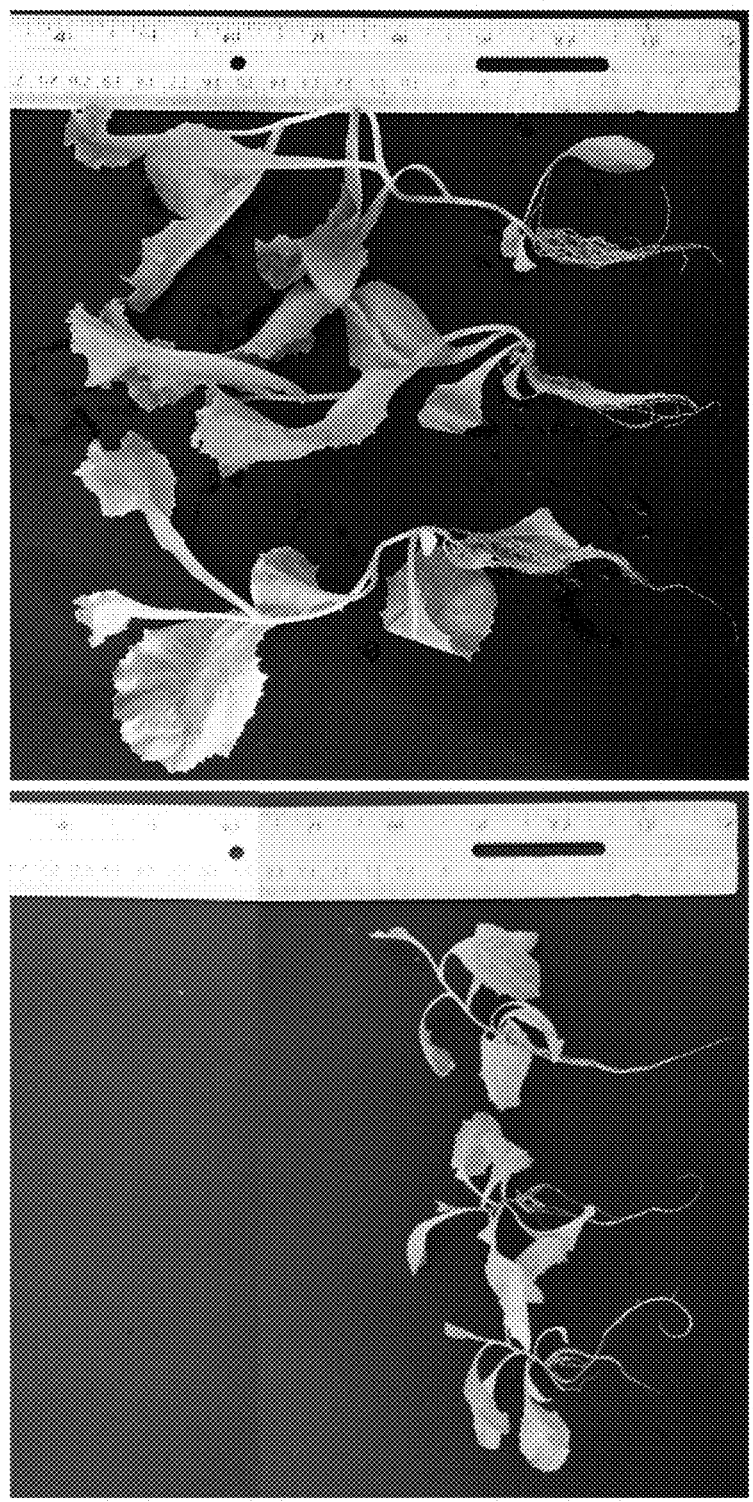

Exemplary FIG. 21 displays plant growth promotion in lettuce (Family Asteraceae, species *Lactuca sativa* cv. Grand Rapids) following exposure in vitro to *C. sp* VOCs. All plants were one month old after sowing.

Figure 22:
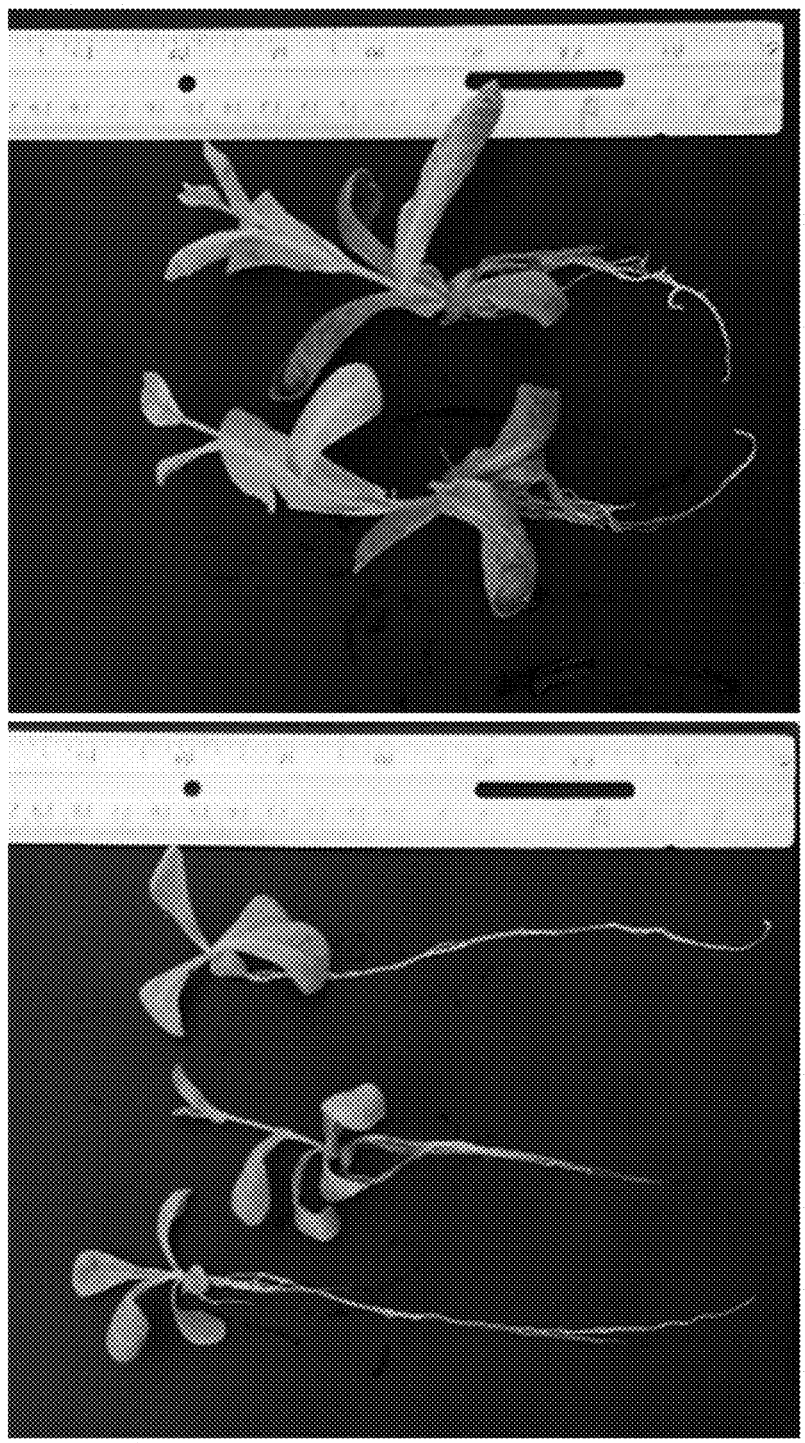

Exemplary FIG. 22 shows plant growth promotion in endive (Family Asteraceae, species *Cichorium endivia* var. *latifolia* cv. Broadleaf Batavian) following exposure in vitro to *C. sp* VOCs. Tissue culture plants without exposure to VOCs were used as control. All plants were one month old after sowing.

Figure 23:
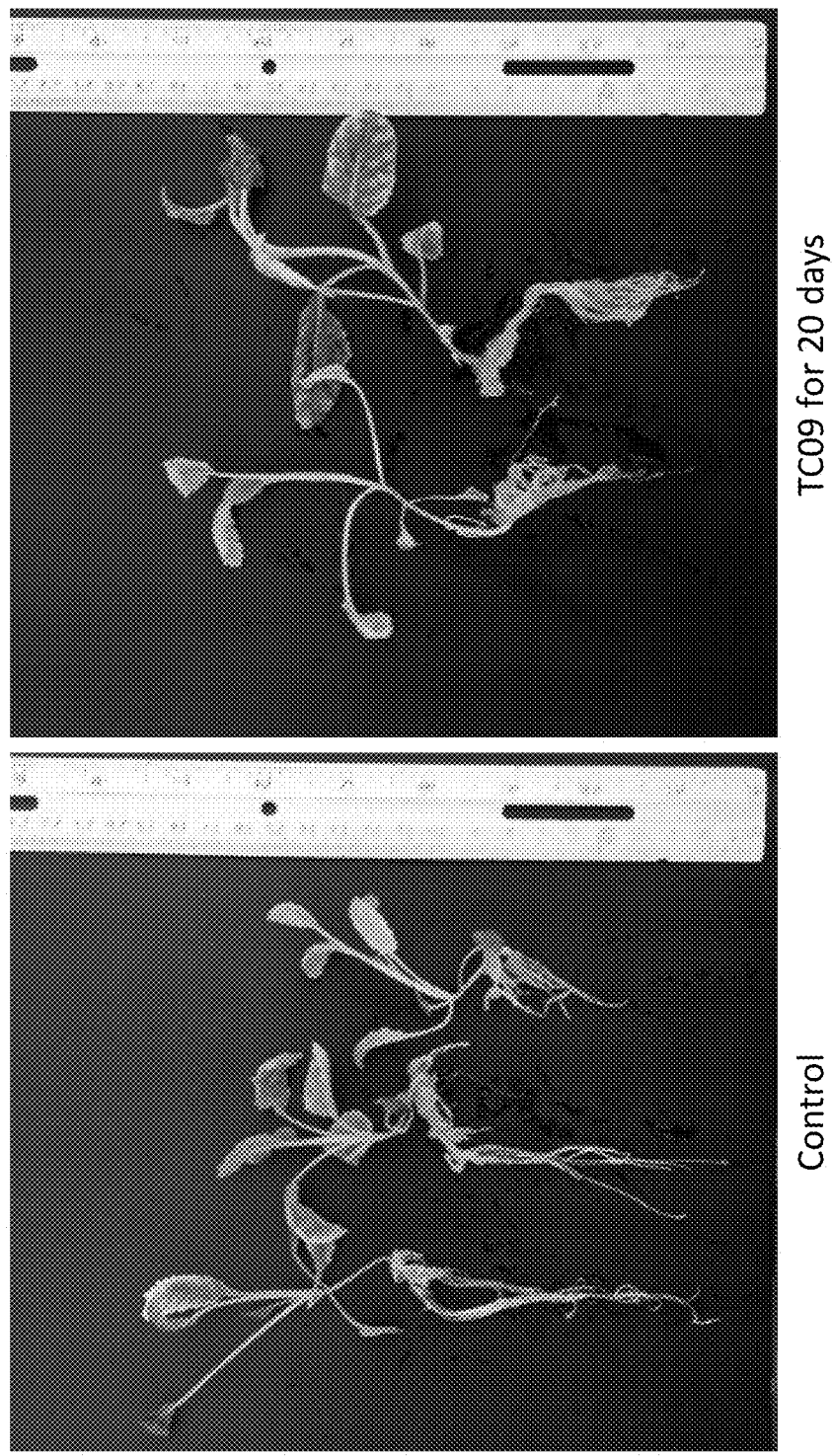

Exemplary FIG. 23 exhibits plant growth promotion in kale (Family Brassicaceae, species *Brassica oleracea* cv. Toscano) following exposure in vitro to *C. sp* VOCs. Tissue culture plants without exposure to VOCs were used as control. All plants were one month old after sowing.

Figure 24:
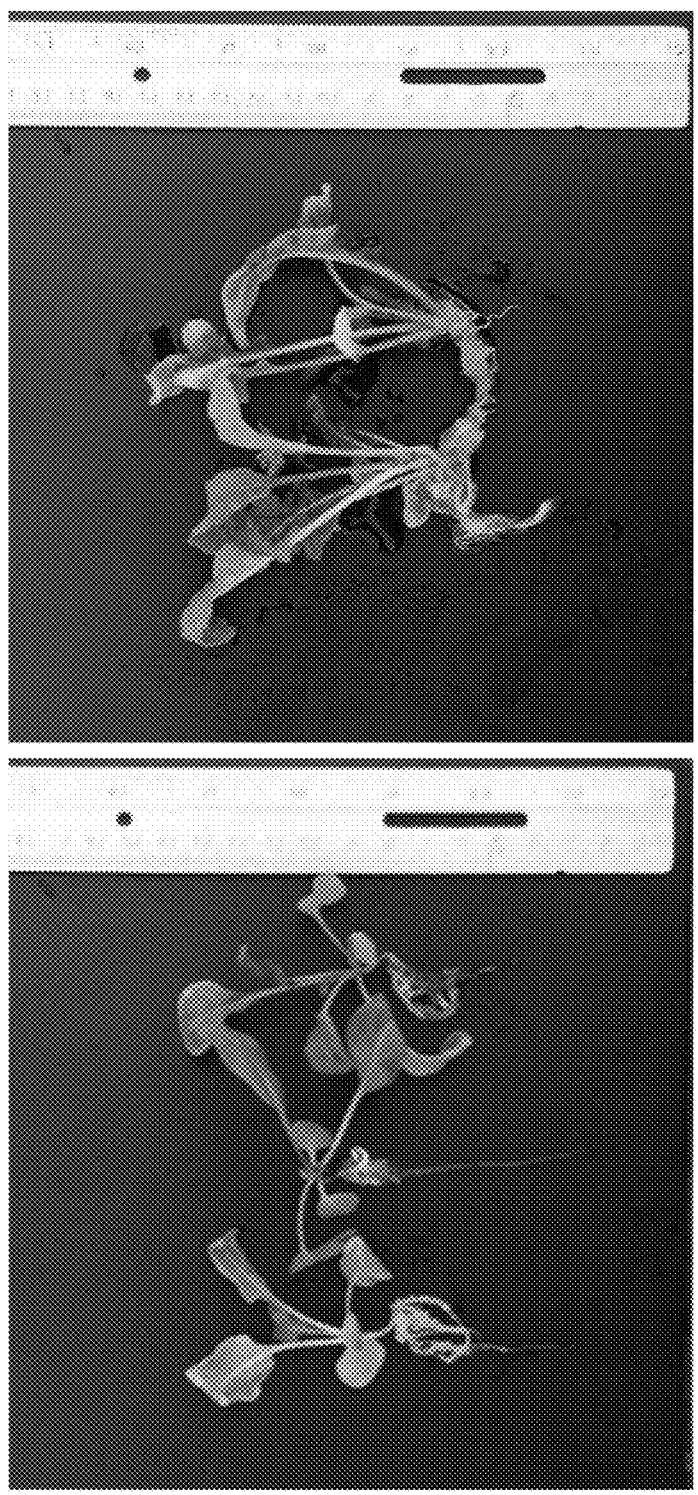

Exemplary FIG. 24 displays plant growth promotion in arugula (Family Brassicaceae *Eruca vesicaria* ssp. *Sativa*) following exposure in vitro to *C. sp* VOCs. Tissue culture plants without exposure to VOCs were used as control. All plants were one month old after sowing.

Figure 25:
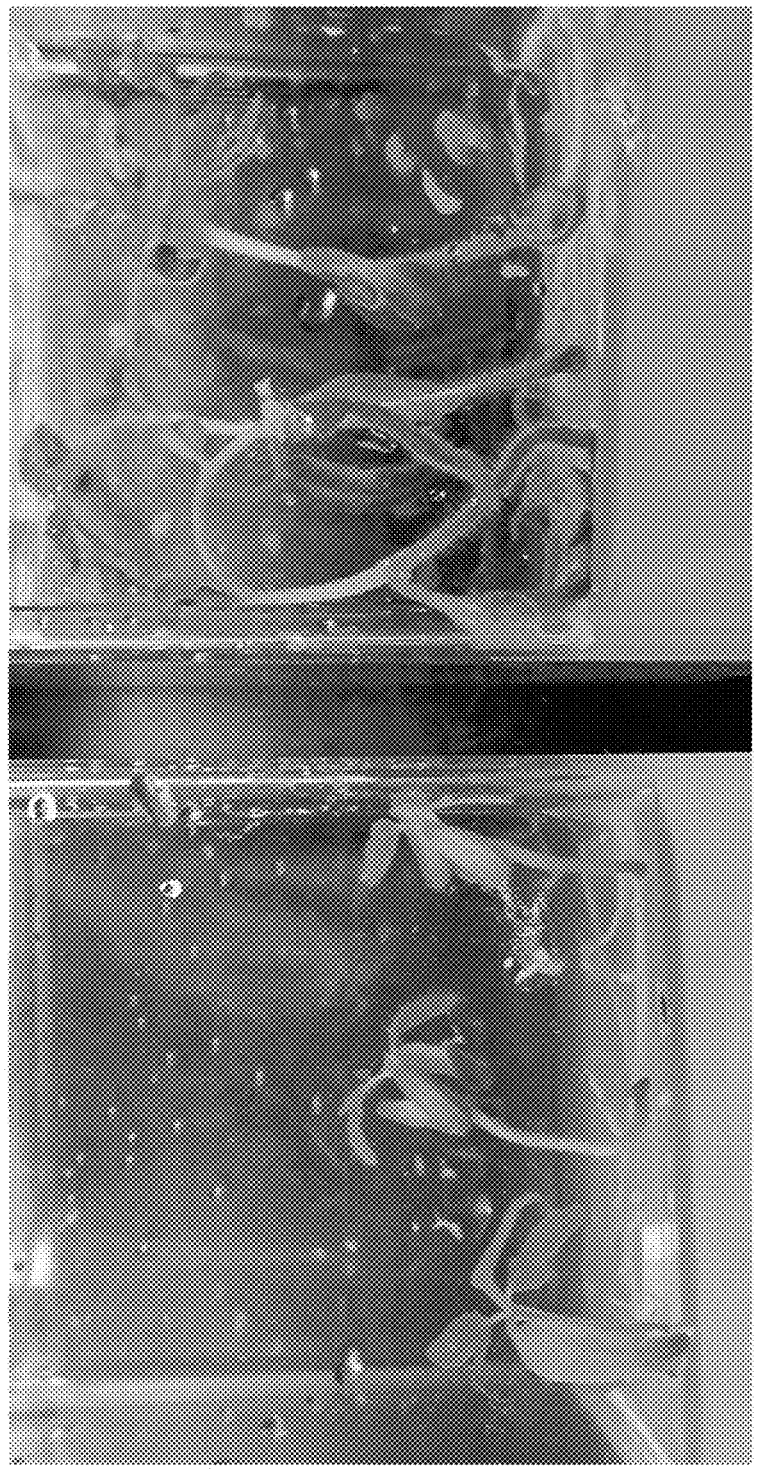

Exemplary FIG. 25 exemplifies plant growth promotion in tomato (Family Solanaceae, species *Solanum lycopersicum* cv. Roma) following exposure in vitro to *C. sp* VOCs. Tissue culture plants without exposure to VOCs were used as control. All plants were 15-day old after sowing.

Statement Regarding Deposit of Biological Material Under the Terms of the Budapest Treaty The inventors deposited samples of *Cladosporium sphaerospermum* as described herein on or before Apr. 19, 2018, with the U.S.D.A., Agricultural Research Service's Patent Culture Collection located at the National Center for Agricultural Utilization Research, 1815 N. University Street, Peoria, Ill. 61604, in a manner affording permanence of the deposit and ready accessibility thereto by the public if a patent is granted. The deposit has been made under the terms of the Budapest Treaty on the International Recognition of the Deposit of Microorganisms for the Purposes of Patent Procedure and the regulations thereunder. The deposits' accession numbers are NRRL 67603 and NRRL 67749. The deposit of *Cladosporium sphaerospermum* represented by NRRL 67603 was deposited on or before Apr. 19, 2018. The deposit of *Cladosporium sphaerospermum* represented by NRRL 67749 was deposited on or before Mar. 7, 2019.

All restrictions on the availability to the public of *C. sphaerospermum* Accession Nos. NRRL 67603 and NRRL 67749 which have been deposited as described herein will be irrevocably removed upon the granting of a patent covering this particular biological material.

The *C. sphaerospermum* Accession Nos. NRRL 67603 and 67749 have been deposited under conditions such that access to the microorganism is available during the pendency of the patent application to one determined by the Commissioner to be entitled thereto under 37 C.F.R. § 1.14 and 35 U.S.C § 122.

The deposited biological material will be maintained with all the care necessary to keep them viable and uncontaminated for a period of at least five years after the most recent request for the furnishing of a sample of the deposited microorganisms, and in any case, for a period of at least thirty (30) years after the date of deposit or for the enforceable life of the patent, whichever period is longer.

We, the inventors for the invention described in this patent application, hereby declare further that all statements regarding this Deposit of the Biological Material made on information and belief are believed to be true and that all statements made on information and belief are believed to be true, and further that these statements are made with knowledge that willful false statements and the like so made are punishable by fine or imprisonment, or both, under section 1001 of Title 18 of the United States Code and that such willful false statements may jeopardize the validity of the instant patent application or any patent issuing thereon.

Also described herein is the use of *C. sphaerospermum* Accession No. NRRL 8131 (previously referenced as *Cladosporium* lignicolum Corda (Dugan, et al., *Persoonia* 21:9-16 (2008)). The NRRL culture 8131 was deposited on or before Nov. 5, 1975 with the U.S.D.A., Agricultural Research Service's Patent Culture Collection. NRRL 8131 is permanently available to the public and may be obtained by writing: ARS Culture Collection, 1815 North University Street, Peoria, Ill. 61604.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

The amounts, percentages, and ranges disclosed herein are not meant to be limiting, and increments between the recited amounts, percentages, and ranges are specifically envisioned as part of the invention.

The term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein.

A novel strain of *Cladosporium sphaerospermum* (also referred to as *C. sphaerospermum* or *C. sp* herein) Accession No. NRRL 67603 has been identified. It is *C. sp* strain TC09. It contains an ITS1/2 consensus amplicon of SEQ ID NO: 5 and an ITS3/4 consensus amplicon of SEQ ID NO: 6. It is also referred to as *C. sp* Accession No. NRRL 67603. Also identified was *C. sp* Accession No. NRRL 67749. These *C. sp* produce MVOCs that, when exposed to a plant, increase at least one of the treated plant's growth characteristics. The growth characteristics include, but are not limited to, growth rates; aerial biomass weight; plant height; number of branches; number of leaves; leaf size, weight, and/or thickness; leaf expansion rate; petiole size/diameter/thickness; stem, branch and/or trunk thickness (caliper), length, weight, and/or elongation; root biomass; types of root; root extension; root depth, weight and/or diameter; root robustness and anchorage; abiotic stress tolerance (cold, heat, salinity and/ or drought); anthocyanin pigment production and accumulation; oil quality; secondary metabolite accumulation; sensory and flavor compound production, fiber hypertrophy and quality; quantity/amount of chlorophyll; photosynthesis rate and/or efficiency; leaf senescence retardation rate; early and efficient fruit set; early fruit maturation; fruit yield; yield of fruit/grain and/or seeds; size and/or firmness of fruit, grain and/or seeds; early flowering (flowering precocity); harvest duration; starch content of fruit, vegetative tissues, grain, and/or seeds; and sugar content of fruit, vegetative parts, root and tubers, grain and/or seeds. An increase in a growth characteristic is an increase in any one of these growth characteristics.

*C. sp* does not need to grow in the soil with the plant; in fact, such growth in soil may result in reduced effects on the plant's phenotype (growth, yield, etc.). *C. sp* can be cultured on solid media sufficiently close of the plant such that the MVOCs are able to reach the plant's headspace and exert a positive impact on the plant's phenotype.

In one embodiment, *C. sp* is growing in such a manner that the MVOCs are released into the headspace of a plant to be treated. In one embodiment, *C. sp* is growing in a container within the headspace of the plant to be treated. In another embodiment, *C. sp* is growing in a container that is connected via one or more tubes, pipes, openings, etc., to the headspace of the plant to be treated. In this embodiment, the MVOCs are able to move from *C. sp* to the container containing the plant to the treated and thus the plant's headspace via the tube(s), pipe(s), opening(s), etc. In one embodiment, headspace is the area around the seed, leaves, branches, and/or roots of a plant to be treated. In another embodiment, headspace is the area around the seed, leaves, and/or branches of a plant to be treated.

While any media can be used, in one embodiment *C. sp* may be grown on Murashige and Skoog (MS) medium (Murashige and Skoog, *Plant Physiol*, 15:473-497 (1962)). In another embodiment, *C. sp* is grown on potato dextrose agar (PDA) medium. In another embodiment, *C. sp* is grown on Czapek-DOX yeast agar (Czapek or CYA) medium. In another embodiment, *C. sp* is grown on malt extract agar (Malt) medium. In another embodiment, *C. sp* is grown on yeast extract (Yeast) medium. In another embodiment, *C. sp* is grown on Hunter's medium. The contents of these media are known to one of ordinary skill in the art and may be purchased from a variety of companies (See, e.g., Sinclair and Dhingra. *Basic Plant Pathology Methods*. CRC Press Inc., Boca Raton, Fla. (1995)).

As used herein, the term "plant" includes reference to whole plants, plant organs (e.g., leaves, stems, roots, etc.), seeds, plant cells, plant germplasms, and progeny of same. The term "plant cell" includes, without limitation, seeds suspension cultures, embryos, meristematic regions, callus tissue, leaves, roots, shoots, gametophytes, sporophytes, pollen, and microspores.

Suitable plants include, without limitation, energy crop plants, plants that are used in agriculture for production of food, fruit, wine, fiber, oil, animal feed, plant-based pharmaceutical and industrial products, medicinal and non-medicinal health-related or recreational products, plants used in the horticulture, floriculture, landscaping and ornamental industries, and plants used in industrial settings. Plants that can be used are of the present disclosure may be gymnosperms and angiosperms, flowering and non-flowering. If an angiosperm, the plant can be a monocotyledon or dicotyledon. Non-limiting examples of plants that could be used include desert plants, desert perennials, legumes, (such as *Medicago sativa*, (alfalfa), *Lotus japonicas* and other species of *Lotus, Melilotus alba* (sweet clover), *Pisum sativum* (pea) and other species of *Pisum, Vigna unguiculata* (cowpea), *Mimosa pudica, Lupinus succulentus* (lupine), *Macroptilium atropurpureum* (siratro), *Medicago truncatula, Onobrychis, Vigna*, and *Trifolium repens* (white clover)), corn (maize), pepper, tomato, *Cucumis* (cucumber, muskmelon, etc.), watermelon, *Fragaria, Cucurbita* (squash, pumpkin, etc.) lettuces, *Daucus* (carrots), *Brassica, Sinapis, Raphanus*, rhubarb, sorghum, *Miscanthus*, sugarcane, poplar, spruce, pine, *Triticum* (wheat), *Secale* (rye), *Oryza* (rice), *Glycine* (soy), cotton, barley, tobacco, potato, bamboo, rape, sugar beet, sunflower, peach (*Prunus* spp.) willow, guayule, eucalyptus, *Amorphophallus* spp., *Amorphophallus konjac*, giant reed (*Arundo donax*), reed canarygrass (*Phalaris arundinacea*), *Miscanthus giganteus, Miscanthus* sp., *sericea lespedeza* (*Lespedeza cuneata*), millet, ryegrass (*Lolium multiflorum, Lolium* sp.), *Phleum pratense* (timothy), *Kochia* (*Kochia scoparia*), forage soybeans, hemp, kenaf, *Paspalum notatum* (bahiagrass), bermuda grass, Pangola-grass, fescue (*Festuca* sp.), *Dactylis* sp., *Brachypodium distachyon*, smooth bromegrass, orchard grass, Kentucky bluegrass, turf grass, *Rosa, Vitis, Juglans, Trigonella, Citrus, Linum, Geranium, Manihot, Arabidopsis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Browaalia, Phaseolus, Avena, Hordeum*, and *Allium*.

In one embodiment, treatment of plants with *C. sp* or its VOCs to achieve growth stimulation is a two process. First, one exposes seedlings following seed germination to MVOC-filled headspace in an enclosed culture setup for a certain period of time (referred to as "exposure duration"). Second, one removes the plants from the MVOC-filled headspace or, alternatively, removes the MVOC-filled headspace from the plants. Either way, the plants are allowed to grow in the desired media, such as soil or non-soil based growth media, for subsequent plant development and production. One can expose the seedlings beginning at less than 1 hour post-germination, at 1, 2, 3, 4, 5, 6, 7, 8, 9, 10, 11, 12, 13, 14, 15, 16, 17, 18, 19, 20, 21, 22, 23, or 24 hours post-germination, or at 1, 2, 3, 4, 5, 6, 7, 8, 9, 10, 15, 20, 25, or 30 days post-germination, or at 1, 2, 3, 4, 5, 6, 7, 8, 9, 10, 11, or 12 months post-germination, or at 1, 2, 3, 4, 5, 6, 7, 8, 9, 10, or more years post-germination. Germination occurs with the emergence of the root and cotyledonary leaves.

The length of time during which a plant is exposed to *C. sp* and/or its VOCs can vary. The exposure duration used can depend on the desired response(s) of target plant species and the age of the target plant species at the time of the exposure. In one embodiment, a plant is exposed to *C. sp* and/or its VOCs for 1, 2, 3, 4, 5, 6, 7, 8, 9, 10, 15, 20, 25, or 30 days or for 1, 2, 3, 4, 5, 6, 7, 8, 9, 10, 11, or 12 months. Older plants (for example, deciduous plants that are more than 1 year old) may need longer exposure time in order to obtain the desired effect compared to younger plants (for example, annual plants that have recently germinated). One can monitor and control the level of growth stimulation while the plant is exposed to *C. sp* and/or its VOCs until desired outcome is achieved. For longer exposure durations, one may need to replace the *C. sp* that is growing within the same headspace as the plant or replace the media on which the fungus is growing so that VOCs are being generated and emitted by the fungus during the entire exposure duration.

While the size of containers selected to provide adequate headspace for MVOC treatment for particular target plant species can be scaled up or down, a typical treatment setup for plant species, such as tobacco, involves the use of a culture vessel that measures 7.5 cm (length)×7.5 cm (width)×10 cm (height), for example, a Magenta™ GA7 vessel (MilliporeSigma, St. Louis, Mo.) for plant culture and a smaller container, such as plastic tube closure that measures 3 cm×4 cm, diameter×height (Sigma C5791, MilliporeSigma, St. Louis, Mo.) for *C. sp* cultivation. The plastic tube closure is used to culture *C. sp* for MVOC emission and placed inside the plant culture vessel. In one embodiment, 10 µl of *C. sp* conidial suspension at a density of $1 \times 10^5$ conidia per ml of water (1000 conidiospores in total) is transferred onto one plastic tube closure. Typically, one such *C. sp* inoculated plastic tube closure is placed in one plant culture vessel, although more than one plastic tube closure can be used to augment the MVOC effects. In another embodiment, 100 µl or a greater volume of *C. sp* conidial suspension at similar density is transferred onto a single plastic tube closure. In yet another embodiment, 10 µl of *C. sp* conidial suspension at a density ranging from $1 \times 10^3$ conidia per ml to $1 \times 10^7$ conidia per ml can be used. In another embodiment, the *C. sp* culture can be grown in a separate container that is connected to the plant-containing culture vessel via tubing or pipes fitted with a sterile aerosol filter to restrict movement of conidia but to provide airborne VOCs to the headspace of the plant containing culture vessel. In such a connective setting, *C. sp* and/or its VOCs from 1000 or more conidia is sufficient to treat plants housed in a vessel/container with a total headspace of 500 to 1000 $cm^3$. In another embodiment containers for *C. sp* culture can be scaled up to gallon pails and large incubators/barrels that are connected to plant containing devices through tubing or pipes or that are placed inside the plant-containing devices.

In another embodiment, other types of containers that have the capacity to hold/culture seedlings and plants can be used to provide headspace needed for MVOC exposure. These other containers include, but are not limited to, jars, glass or plastic containers/trays in various sizes and shapes, a tent, a tunnel, a man-made or manufactured box, a greenhouse, a cabinet, an incubator, a room or rooms, and a building.

While aerial delivery of MVOCs to aboveground plant tissues is achieved through headspace, the delivery of MVOCs to lower or underground parts of the plant, such as roots, can also be implemented to achieve growth stimulation. In such a setting, a hole can be punctured through the aerial portion of the container in which *C. sp* is grown and a hole can be made through the side or bottom of a container/pot that houses plants or seedlings to be treated. Tubing or pipes can be fitted to connect these two containers to allow movement of VOCs from the *C. sp* culture to the root. MVOCs have the ability to penetrate liquid or semi-solid culture medium and reach root cells to effect plant growth. In other words, any conceivable delivery devices that can be constructed to deliver MVOCs to plant cells can be used for *C. sp* and its VOCs.

In any of the above-mentioned settings, normal growth of *C. sp* may be maintained to provide a consistent and continuous supply of VOCs. In one embodiment, replacement of fresh cultures can be made if culture media become overly dry thereby limiting fungal growth. In another embodiment, lighting is not required for fungal growth. *C. sp* growth can be maintained under either light or dark conditions. In yet another embodiment, ambient temperature (approx. 15° C. to approx. 28° C.) is used to culture *C. sp*.

*Cladosporium* fungi are well known for their vulnerability to high temperatures and can lose vitality when exposed to 45° C. or higher for a few minutes. Thus, in another embodiment, one cultures *C. sp* between approximately 15° C. and approximately 40° C. UV light is highly mutagenic to fungi and may alter the genetic milieu and performance of *C. sp* and/or its VOCs. Thus, in one embodiment, *C. sp* is cultured in light with wave lengths between 400 nm and 700 nm. In an embodiment, during VOC treatment, especially with extended exposure durations, plants should be managed properly to minimize influence from abiotic stresses, such as, overheating, cold, drought, lack or depletion of nutrients/fertilizers, lack of proper illumination/sunlight, and/or over-accumulation of moisture and phytotoxic compounds that adversely affect normal plant growth. Practitioners skilled in the art of growing plants understand the conditions necessary to grow and maintain plants while the plants are receiving VOC treatment.

Upon exposure to *C. sp* and/or its VOCs, one or more of the plant's growth characteristics are improved within a short period of time. In one embodiment, within 12 hours after initial exposure to *C. sp* and/or its VOCs, plants can have thickened petiole, enlarged leaf size, increased amount of anthocyanin pigment production and accumulation, root extension, and stem elongation, to name a few. In another embodiment, tobacco seedlings exposed to *C. sp* and/or its VOCs produce unique circular and robust roots within 2 days after initial exposure while roots from non-exposed tobacco plants remain straight and short. In another embodiment, tobacco plants exposed to *C. sp* and/or its VOCs for 24 hours initiated after germination of the plants and then allowed to grow without additional exposure to the VOCs for another 3 weeks exhibit twice the plant size as negative control tobacco plants. In another embodiment, tobacco plants exposed to *C. sp* and/or its VOCs for 10 to 20 days starting after germination have a stem length that is approximately 15-fold to approximately 120-fold greater than the stem length of negative control tobacco plants. Total plant biomass of tobacco plants exposed to *C. sp* and/or its VOCs also is approximately 10-fold to 15-fold greater than the biomass of negative control tobacco plants. In another embodiment, at least one growth characteristic increases when a plant is being exposed for a short duration (as discussed above) to *C. sp* and/or its VOCs or at least one growth characteristic increases after removal of VOC treatment from the treated plant. Exposure of a young plant (or seedling) to *C. sp* and/or its VOCs for 1, 2, 3, 4, 5, 6, 7, 8, 9, 10, 11, 12, 13, 14, 15, 16, 17, 18, 19, 20 days, or longer causes the treated plant to have an increase in at least one growth characteristic for the life of the plant or for the growing season of the plant. Note that "1 day" is an approximation; it includes 23 hours, 22 hours, 21 hours, 20 hours, and even approximately 19 hours. Exposure does not need to be continuous but can occur with a period of non-exposure in-between the exposures.

Exposure to *C. sp* and/or its VOCs may have long lasting effects on a plant's growth characteristics after exposure to the VOCs is terminated. In one embodiment, at least one growth characteristic of an exposed plant increases (compared to the same growth characteristic of an unexposed plant) after the exposed plant is transferred to soil or other growth media and maintained in an open environment, such as, a greenhouse, screenhouse, tunnel, or field (that is, exposure to the MVOCs are terminated). In one particular embodiment, pepper plants exposed to *C. sp* and/or its VOCs produce fertile flowers about 20 days earlier than negative control pepper plants without exposure to *C. sp* and/or its VOCs and derived from either direct seedling or tissue culture process. In another embodiment, at 140 days after seed sowing, cayenne pepper plants exposed to *C. sp* and/or its VOCs produce approximately 5 times more pepper fruit than produced by negative control cayenne pepper plants (not exposed to *C. sp* and/or its VOCs). In another embodiment, at 160 days after direct seeding, mini sweet pepper plants exposed to *C. sp* and/or its VOCs produce approximately 170% more vine-ripe pepper fruit than negative control mini sweet pepper plants. In yet another embodiment, fruit harvested from mini sweet pepper plants exposed to *C. sp* and/or its VOCs have approximately 20% increase in average ° Brix value (a measurement of sugar content in fruit juice) than fruit harvested from negative control mini sweet pepper plants, both experimental and negative control plants are derived from either direct seeding or tissue culture.

Having now generally described this invention, the same will be better understood by reference to certain specific examples, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1: Fungal Identification

An unknown fungus was found growing as a contaminant on Murashige and Skoog (MS) medium tissue culture plates. Tobacco plants growing on the contaminated plants were larger than similarly aged tobacco plants grown on non-contaminated plates. Because it was presumed that the fungus caused the tobacco plants to gain more biomass than the non-treated plants, experiments were undertaken to identify the specific fungal genus and species. A culture was grown on MS medium in Petri plates at 25° C. Fungal spores were collected from the culture and kept in a 1.5 mL microcentrifuge tube at −20° C. Genomic DNA was isolated using the DNEasy Plant Mini Kit (Qiagen, Germantown, Md.). Briefly, microcentrifuge tubes containing conidia were removed from the freezer, and liquid nitrogen was added to the microcentrifuge tubes. The tissue was ground using a motorized pestle mixer (VWR Pellet Mixer, VWR, Intl., Radnor, Pa.). The DNA was isolated following the manufacturer's protocol with one exception; in the final step, DNA was eluted from the spin column using 100 μL warmed (65° C.) nuclease-free water. Concentration was determined with a Qubit® 2.0 fluorometer and the dsDNA HS Assay Kit (Thermo Fisher Scientific, Waltham, Mass.). Conventional polymerase chain reaction (PCR) was performed using the genomic DNA as a template. Two reactions, containing internal transcribed spacers 1 and 2 (ITS1/2) primer pairs or containing ITS3 and ITS4 (ITS3/4) primer pairs, were conducted in a Bio-Rad thermocycler with 60° C. annealing temperature. Sequences of the primer pairs are as described by White, et al. (*PCR Protocols: A Guide to Methods and Applications*, 1st ed. Academic Press, New York, pp. 315-322 (1990)): forward primer ITS1, 5'-TCCGTAGGT-GAACCTGCGG-3' (SEQ ID NO: 1); reverse primer ITS2, 5'-gctgcgttcttcatcgatgc-3' (SEQ ID NO: 2); forward primer ITS3, 5'-GCATCGATGAAGAACGCAGC-3' (SEQ ID NO: 3); reverse primer ITS4, 5'-ggaagtaaaagtcgtaacaagg-3' (SEQ ID NO: 4). Both amplicons were visualized on a gel with ethidium bromide, single products were purified using Qiagen PCR clean up kit, and quantified using a Nanodrop spectrophotometer. Products were submitted for Sanger sequence analysis at Eurofins Inc. and data was analyzed using Geneious software (Biomatters, Ltd., Auckland, NZ). The 138 bp ITS1/2 2× consensus amplicon sequence was analyzed using MegaBLAST and was found to be 100% identical to *Cladosporium sphaerospermum* isolate UACH-124 Genbank Accession number KU926349.1, and the 249 bp ITS3/4 2× consensus sequence was 100% identical to *Cladosporium sphaerospermum* strain 7 Genbank accession number KX982238.1. The 138 bp ITS1/2 consensus amplicon has the following sequence: GGCCGGGGATGTTCAT-AACCCTTTGTTGTCCGACTCTGTTGCCTCCGGGGC GACCCTGCCTTTTCACGGGCGGGGGCC CCGGGTGGACACATCAAAACTCTTGCGTA ACTTTGC AGTCTGAGTAAATTTAATTAATAA (SEQ ID NO: 5). The 249 bp ITS3/4 consensus amplicon has the following sequence: TTCAGTGAATCATCGAATCTTT-GAACGCACATTGCGCCCCCTGGTATTCCGGGGGGC ATGCCTGTTCGAGCGTCATTTCACCACT-CAAGCCTCGCTTGGTATTGGGCGACGCGG TCCGCCGCGCGCCTCAAATCGACCGGCTGGG TCTTCTGTCCCCTCAGCGTTGTGGAAACTAT-TCGCTAAAGGGTGCCACGGGAGGC-CACGCCGAAAAACAAACCCATTTCTAA GGTTGACCTCGGATCAGGTAGG (SEQ ID NO: 6). Phylogenetic analysis with more than 148 ITS3/4 amplicon-like sequences available in Genbank database showed that the isolate belongs to the monophyletic taxon *C. sphaerospermum*. The genetic relationship of the isolated strain of *C. sphaerospermum* to other *C. sphaerospermum* strains is unknown.

Example 2: Characterization of *C. sphaerospermum* VOCs on Tobacco Growth Using Filter-Sealed Microcentrifuge Tubes Initial studies using this uncharacterized *C. sp* Accession No. NRRL 67603 had only been observational, thus controlled replicated studies on plant growth promotion potential were performed. Given the apparently strong response observed in tobacco (*Nicotiana tabacum* cv. Samsun), this system was used to confirm, quantify, and investigate the growth stimulation phenomenon. For in vitro testing, sterilized seeds were utilized.

Premade medium powder containing MS basal salts and MS vitamins (M519) was purchased from Phytotechnology Laboratories (Overland Park, Kans.). For culturing tobacco, a MS medium containing full strength of MS medium powder, 30 g/L or 3% (w/v) sucrose (Sigma Aldrich, St. Louis, Mo.) and 7 g/L gelling agar (Sigma Aldrich, St. Louis, Mo.) was prepared. The pH was adjusted to 5.8 with 1N KOH prior to addition of gelling agar and autoclaving at 121° C. for 20 min. An aliquot of 100 ml of warm culture medium was poured to each Magenta™ GA7 vessel (MilliporeSigma, St. Louis, Mo.).

Mature seeds of tobacco (*Nicotiana tabacum* cv. Samsun) were collected from self-pollinated plants that had been maintained in the greenhouse. They were heated at 50° C. overnight to break weak dormancy. Sterilization of seeds was carried out by soaking briefly in 95% ethanol and then immersed in 20% (v/v) bleach (8.25% w/v sodium hypochlorite) with agitation for 10 min followed by three rinses with sterile water. Seeds were then spread evenly onto Petri plate (15×100 cm) containing 30 ml of MS medium. Cultures were maintained at 25° C. under 16-h photo-cycle light conditions (50 µmol/(m² s¹)) for 6 days. Germinated seeds with expanded cotyledonary leaves and uniform growth status were then utilized in subsequent experiments. Tobacco seeds are small and contain less nutritional reserves, hence it takes a longer time (compared to other types of plants) to develop seedlings with visible green cotyledonary leaves (2-3 mm in length) that can be used as a basis to determine plant uniformity and eliminate abnormality. In general, about 90% of the sowed seeds were viable with a slightly lesser number of seedlings suitable for experimental use.

For initial experiments, fungal cultures were physically separated from plant materials but were sealed with biological filters to avoid spore release (but not MVOCs release). Aliquots of 300 µl warm MS medium was poured into sterile 1.5 ml microcentrifuge tubes. Tubes were then positioned horizontally to form a slant surface. Ten µl of fungal conidial suspension at a density of 1×10⁵ CFU per ml was introduced into each tube, and the tubes were plugged using a sterile aerosol substance- and liquid-resistant filter (Rainin #17001945, Mettler Toledo, Oakland, Calif.). The preparation of *C. sp* Accession No. NRRL 67603 cultures was carried out under aseptic conditions so that culture caps could be placed in Magenta™ vessels without causing external contamination. *C. sp* Accession No. NRRL 67603 conidia were used immediately or stored in clean containers for subsequence use within a time period of up to one month.

One-week old, germinated tobacco seeds were placed in Magenta™ GA7 vessels containing full-strength MS medium with 3% sucrose. Two filter-sealed fungus-containing tubes were inserted at two separate corners in culture vessels. Plants were then maintained under light conditions with a 16-hour photoperiod at 25° C. Plant growth was monitored and compared with growth of control plants that lacked fungal cultures in the vessels (i.e., uninoculated microcentrifuge tube was added to plant growth chamber). Plants were monitored for growth stimulation either with 10-days or 21-days exposure time period. Plant measurements were taken at the end of 20 days after introduction of fungal cultures regardless of exposure duration. A time period of MVOC exposure for 20 days is commonly used in other reported culture experiments; see Paul and Park (2013). Experiment was conducted in triplicate.

The incorporation of filter-sealed *C. sp* Accession No. NRRL 67603 cultures placed into tobacco culture vessels produced markedly positive effects on plant growth characteristics. Relative to negative control plants, the plants incubated with sealed *C. sp* Accession No. NRRL 67603 cultures for 5 days developed thicker stems, larger-sized and thicker leaves, and a more robust root system. By the tenth day, visual observations indicated *C. sp* Accession No. NRRL 67603-exposed plants were several times larger than negative control plants (FIG. 1). During these experiments, no fungal contamination was found in all tobacco culture vessels that harbored filter-sealed *C. sp* Accession No. NRRL 67603 cultures, suggesting that no conidia were able to escape through the filter device and that plant growth stimulation resulted from MVOC activities.

Example 3: Characterization of *C. sphaerospermum* VOCs on Tobacco Growth Using Plastic Culture Tube Closures In vitro containment conditions for fungal cultures were modified to utilize culture tube closure or cap (3×4 cm, diameter×length, closure for 25 mm culture tubes, Sigma C5791) in order to mitigate problems related to condensation build-up inside the filter-sealed microcentrifuge tubes that could suffocate growing fungus and reduce MVOC emission, as subsequently noticed. For each sterile closure cap, 5 ml semi-solid MS medium was added and 10 µl of conidial suspension at a density of 1×10⁵ CFU per ml was subsequently introduced. The fungal culture in the closure was then placed in a Magenta™ GA7 vessel that contains tobacco seedlings. For controls, a blank culture cap was added. All experiments were repeated three times. Each involved three treated and untreated vessels, respectively, and three replicate plants for each vessel. Cultures were placed under light conditions with a 16-h photoperiod at 25° C. Plants were treated with 10 or 20 d of fungal exposure duration. Regardless of exposure duration used, plant growth was monitored and compared with controls without fungal cultures at the end of 20 d after introduction of fungal cultures. For polar auxin transport interference tests, 10 µM auxin transport inhibitor N-1-naphthylphthalamic acid (NPA) is incorporated in plant culture medium and used to assess plant response in the presence of MVOCs.

Figure 2:
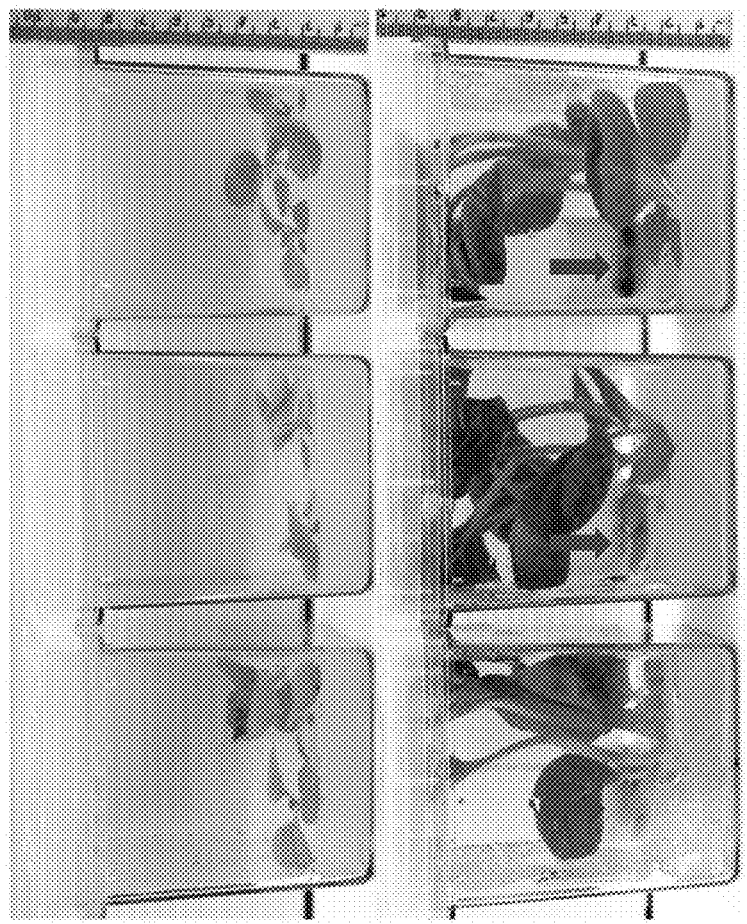
Figure 3:
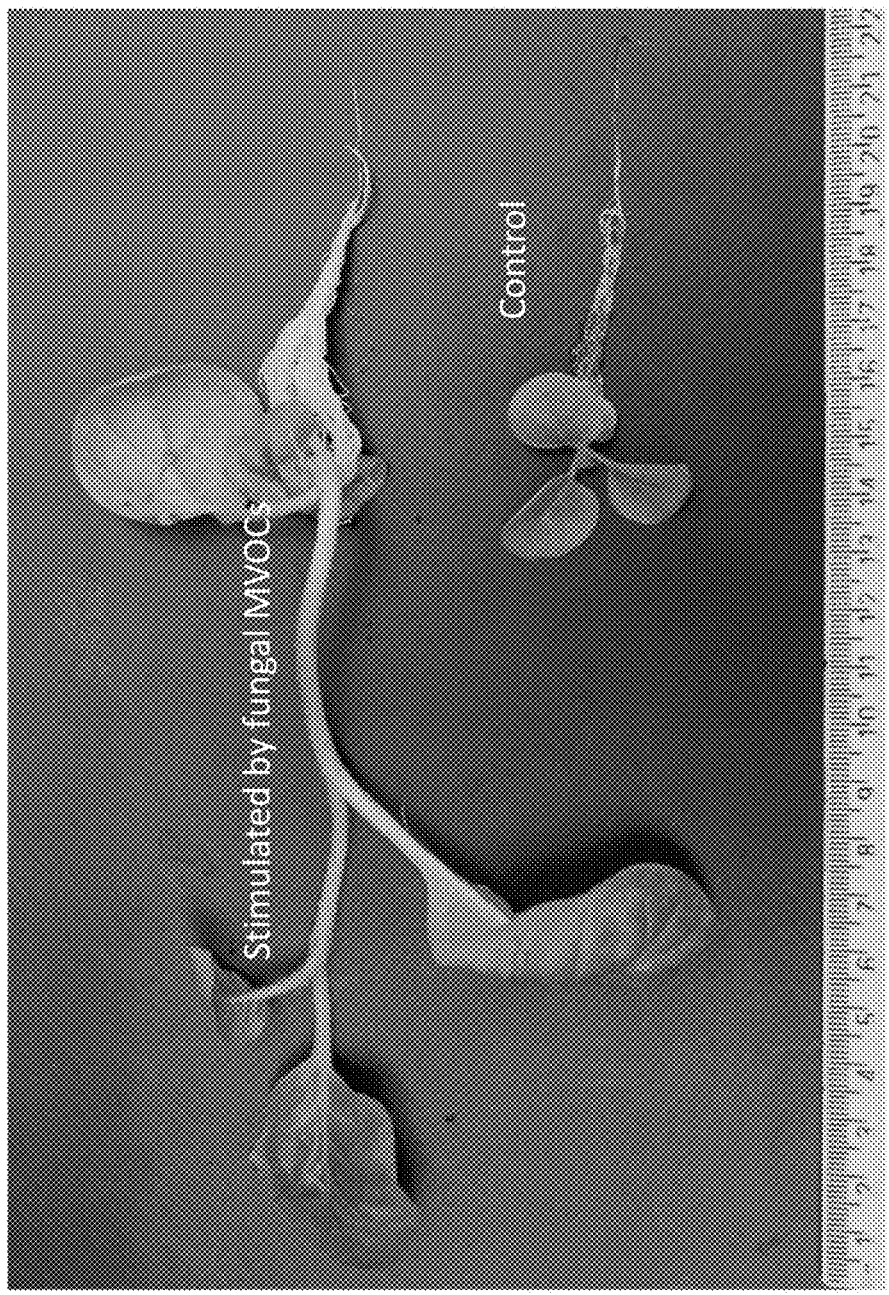
Figure 4:
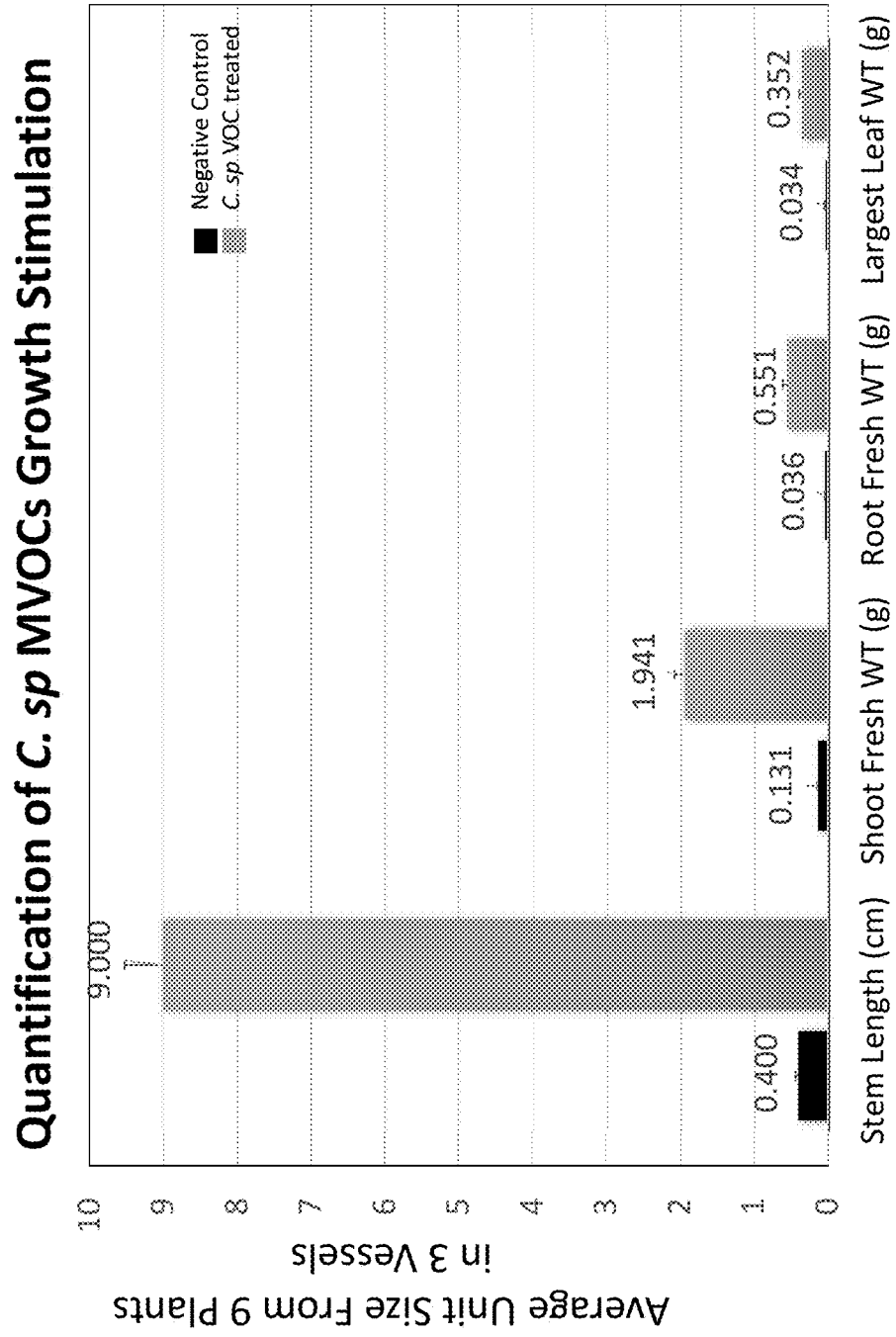
Figure 5:
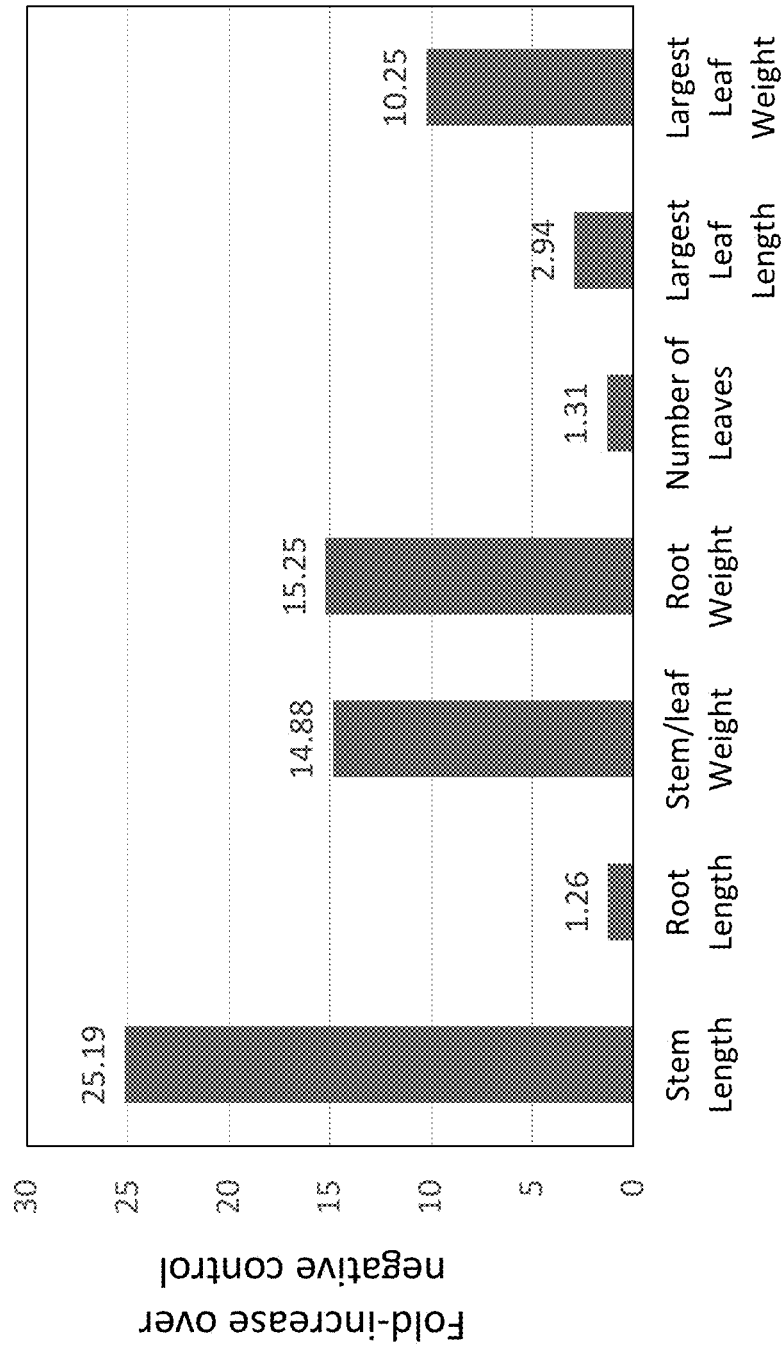

Dramatic differences in multiple plant growth characteristics were observed between 9 treated tobacco plants in 3 replicate vessels treated plants after 20-day exposure to *C. sp* Accession No. NRRL 67603 and similar number of untreated tobacco plants of the same age using the plastic closure-mediated protocol described above. Substantial differences in stem length, shoot (above root base portion) fresh weight, root fresh weight and the width of the largest leaf of each plant were quantified (FIGS. 2, 3, and 4). Data were converted to fold increase over negative control tobacco plants to give the following: approximately 25 fold increase in stem length, approximately 15 fold increase in shoot biomass (shoot/leaf weight; aerial biomass), approximately 15 fold increase in root biomass, and approximately 10 fold increase in weight of largest leaf. See FIG. 5. Root length, number of leaves and largest leaf length all revealed relatively smaller increases of the treated tobacco plants compared to the negative control tobacco plants (FIG. 5).

Figure 6:
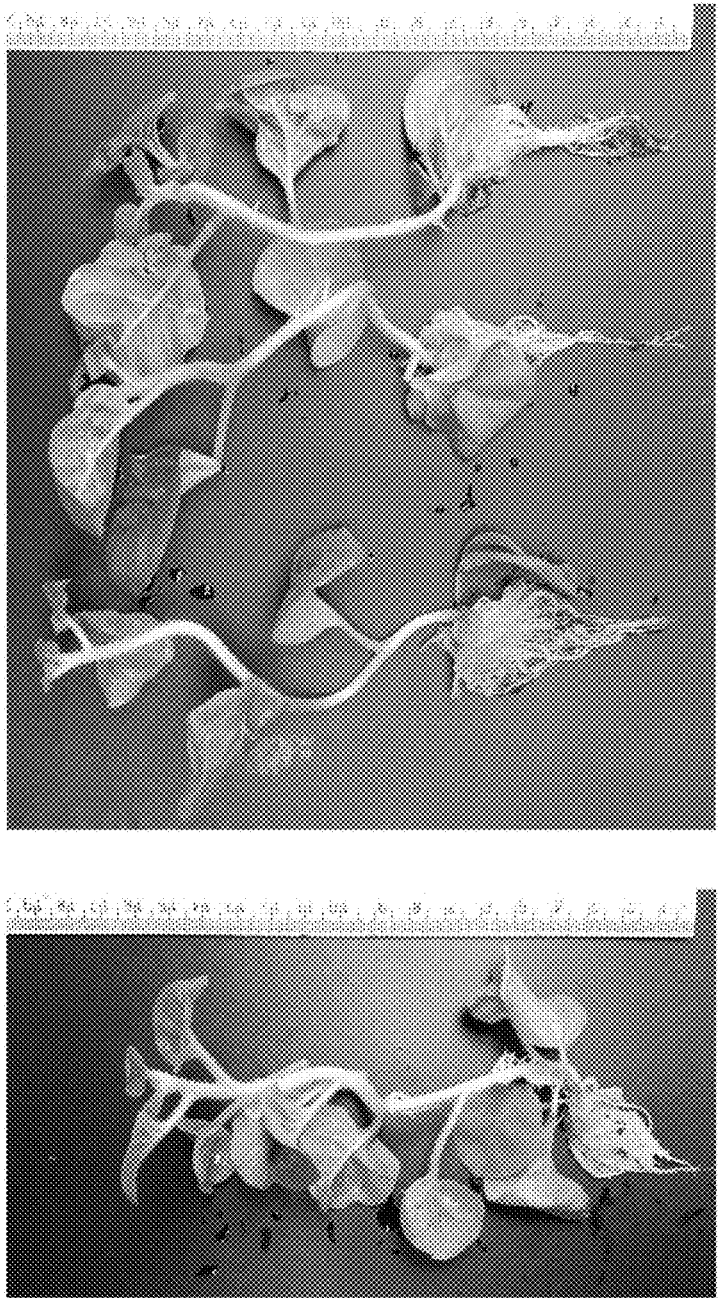
Figure 7:
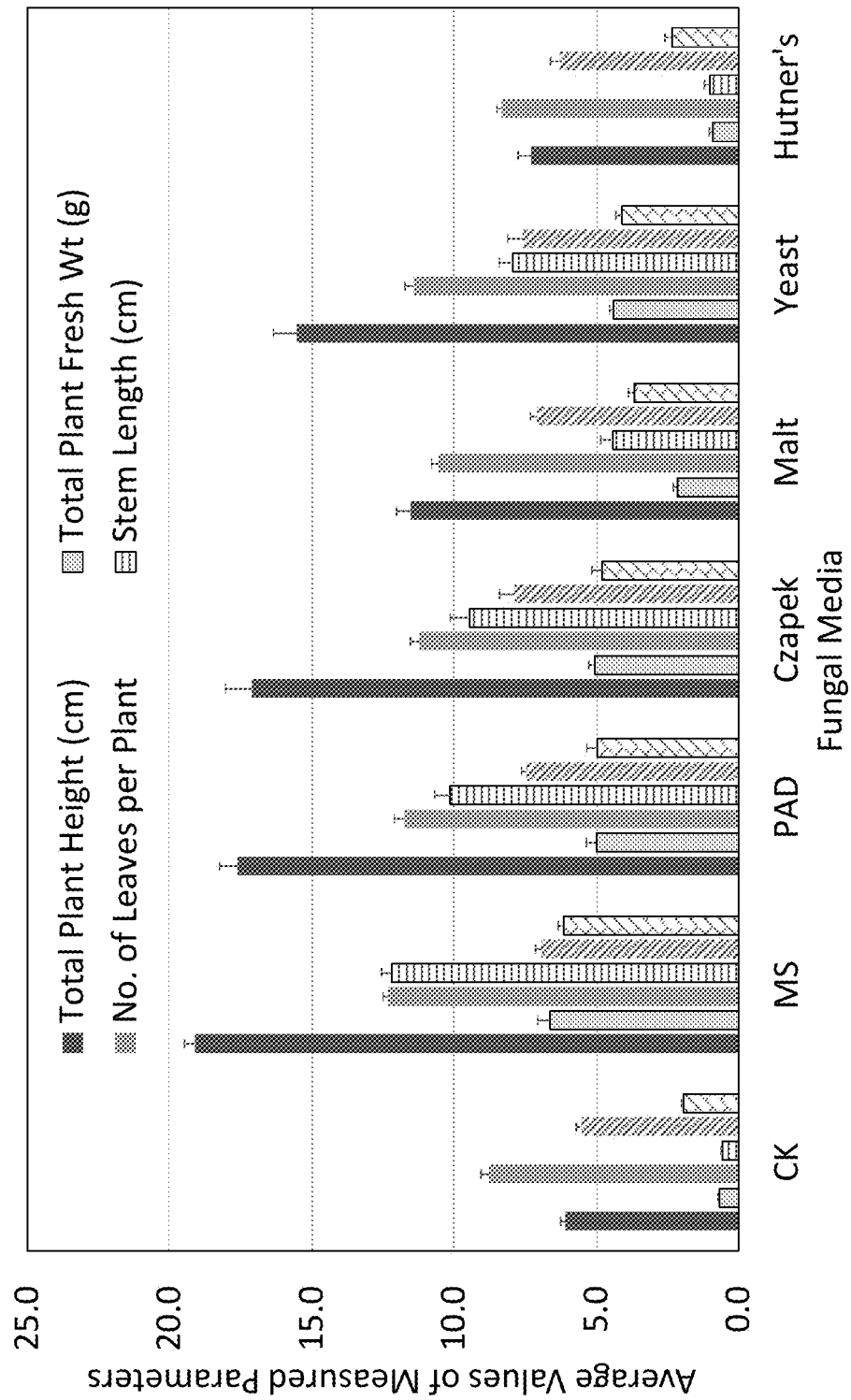

The amount of time for negative control tobacco plants to reach the approximate height and weight observed in 30-day old tobacco plants treated with *C. sp* Accession No. NRRL 67603 for 1 week under tissue culture conditions was measured. As illustrated in FIG. 6, a relative growth differential of two and a half months was observed. At that stage, the negative control 72-day old tobacco plants had developed about 16 leaves, whereas about 10 leaves were formed on the treated 30-day old tobacco plants. The leaf number per plant was recorded based on periodic observations using a 5× magnifier. (Note: Some leaves are very small and hard to see from the figure at the end of the experiment. The leaf number was obtained based on inspections with a magnifier.) This data demonstrates that *C. sp* Accession No. NRRL 67603 VOCs cause accelerated growth in exposed plants.

Example 4: *C. sphaerospermum* Growth Promotion Activity Under Various Growth Medium Conditions It is well known that microbes maintained under different growth environments are able to alter their metabolic/catabolic behaviors and metabolite profiles. To determine if different growth environments can influence *C. sp* Accession No. NRRL 67603 plant growth promoting MVOC production and activity, a number of common fungal media types along with the MS (Murashige and Skoog, *Physiol. Plant* 15:473-497 (1962)) medium were used in this experiment. Besides MS medium, PDA (potato dextrose agar), Czapek (CYA, Czapek-DOX Yeast agar), Malt (Malt extract agar), yeast (Yeast extract extract) and Hunter's medium were tested. Germinated tobacco seedlings (6 days after sowing) were cultured on MS medium containing 3% (w/v) sucrose without any growth regulators in Magenta™ vessels. Flat bottom plastic closure (3 cm×4 cm, dimeter×height) containing one of six different fungal media and *C. sp* Accession No. NRRL 67603 inoculum (10 μl of conidial suspension at $1\times10^5$ CFU per ml) were added to the Magenta™ boxes. After culture under light (16 hour photoperiod) at 25° C. for 20 days, fungal cultures were removed and tobacco plant growth parameters were measured. Essentially, plant and fungal cultures were set up as previously described with the exception that different media were used/tested for fungal culture Similar procedures were also followed for growth measurements.

Results indicated that based on stem height, total plant fresh weight, total plant height and largest leaf length, the order of growth stimulation from highest to lowest among tested culture media for *C. sp* Accession No. NRRL 67603 ranged as follows: MS>PDA>Czapek>Yeast>Malt>Hunter's. See FIG. 7 where "CK" is negative control. MS was the most effective medium while Hunter's medium, which contains rich vitamins and the same amount of sucrose as MS, produced the lowest level of plant growth stimulation.

Example 5: Polar Auxin Transport Plays a Minor Role in *C. sphaerospermum* VOCs Induced Growth Stimulation Auxin is a plant hormone that is critical for many growth and development processes. The auxin polar transport inhibitor N-1-naphthylphthalamic acid (NPA) is commonly used to evaluate the role of auxin in various growth and development pathways because NPA blocks the polar movement of auxin from the shoot, the biosynthesis site, into the root, thus arresting root formation and altering the timing of lateral root development. NPA at a concentration as low as 5 μM is capable of completely negating the stimulatory effects of MVOCs from *Fusarium oxysporum* on plant biomass increase. See, Bitas, et al., *Frontiers in Microbiol* 6:1248 (2015). To assess the involvement of auxin in the effect of the VOCs produced by *C. sp* Accession No. NRRL 67603, six-day old tobacco seedlings where exposed to nothing (negative control), *C. sp* Accession No. NRRL 67603 VOCs ("*C. sp*"), or *C. sp* Accession No. NRRL 67603 VOCs and NPA at a concentration of 10 μM ("10 μM NPA+*C. sp*") in culture medium for 20 days using the protocols described above. NPA displayed arrested lateral root formation. However, these treated plants displayed thickened primary roots relative to controls without NPA and *C. sp* Accession No. NRRL 67603 exposure. NPA plus *C. sp* Accession No. NRRL 67603 treated plants showed significant shoot growth stimulation relative to negative control plants without MVOC treatment but below the levels observed with *C. sp* Accession No. NRRL 67603 treatment alone.

Major growth parameters of the two types of *C. sp* Accession No. NRRL 67603-treated plants indicated that the incorporation of 10 μM NPA reduced the effect of *C sp* Accession No. NRRL 67603 exposure on stem length, shoot/leaf weight, root weight and largest leaf weight by approximately 50 to approximately 60%, while root length, number of leaves and largest leaf length remained similar (FIG. 8 in which amounts of change are shown as fold-increase over the indicated measurements of negative control plants).

Without wishing to be bound to any particular hypothesis, these experiments suggest that simple auxin-induced growth stimulation may be directly or indirectly involved, however it is not the only mechanism involved in *C. sp* Accession No. NRRL 67603 MVOC's plant growth promotion effect.

Example 6: *C. sphaerospermum* Induced Plant Growth is Maintained after Transfer to Soil Experiments were conducted to determine if tobacco plants stimulated by *C. sp* Accession No. NRRL 67603 under culture conditions would maintain growth promotion after the removal of *C. sp* Accession No. NRRL 67603 treatment (exposure to *C. sp* Accession No. NRRL 67603 VOCs) and transfer of treated tobacco plants to soil. In vitro tobacco plants following exposure treatment with or without *C. sp* Accession No. NRRL 67603 MVOCs, using the protocols described above, were transplanted to potting soil mix and maintained in the greenhouse.

For plant establishment in potting soil, Metro Mix 360 or M540 (Sun Gro Horticulture, Elizabeth City, N.C.) was mixed according to manufacturer instructions and sterilized by autoclaving at 121° C. for up to 90 minutes. Cooled soil mix was then used for transplanting. The tobacco plants were maintained in a temperature-controlled greenhouse. Watering and applications of fertilizers were carried out according to standard management practice. Measurement data related to plant growth and development were taken periodically. To determine plant dry weight, tobacco plants were washed carefully to remove all soil matter and air-dried in a temperature-controlled oven equipped with a blower for one week. Data were analyzed using standard statistical approaches. Transplanted *C. sp* Accession No. NRRL 67603 treated tobacco plants displayed sustained growth enhancements in the greenhouse compared to the negative control tobacco plants. Plant height and leaf size were continuously measured for 40 days after transplanting to soil.

*C. sp* Accession No. NRRL 67603 treated plants remained larger than negative control plants throughout the study and retained higher rates of plant height increase and leaf production (FIGS. 9A and 9B). By the $70^{th}$ day after seed sowing, *C. sp* Accession No. NRRL 67603 treated plants produced more than twice the plant height and 25% larger leaves as negative control plants without fungal exposure (FIGS. 9A and 9C). Because of the negative effects of transplant shock, negative control tobacco plants lost some leaves and consequently registered a lower number of visible leaves. On the other hand, no such reduction was found among *C. sp* Accession No. NRRL 67603 treated tobacco plants which steadily increased the number of leaves after transplanting (FIG. 9B).

Example 7: *C. sphaerospermum* Accession No. NRRL 67603 Growth Stimulation in Tobacco Plants Grown and Treated Under Soil Conditions To test whether growth stimulation could be achieved using tobacco plants grown directly in soil (rather than tissue culture conditions), a study was conducted using tobacco plants that were germinated in 4 inch pots arranged in plastic trays containing sealed clear plastic lids (18 plants per tray). Plant exposure to MVOCs was accomplished by placing fungal culture-containing tubes in 6 empty 4 inch pots among 12 plant-containing pots inside a covered large tray (12 inch×23 inch, width×length). *C. sp* Accession No. NRRL 67603 cultures were grown in capped 50 ml plastic tubes containing 10 ml MS medium. MVOCs were allowed to release into the headspace of the covered tray from the enclosed culture tube through a pipette tube that was inserted half-way deep into the tube cap and sealed with biological filters. The 50 ml plastic tubes harboring *C. sp* Accession No. NRRL 67603 cultures were removed after 2 weeks, and plant growth was monitored for an additional two weeks.

Treated tobacco plants showed some growth promotion activity of the shoots, although it was much reduced when compared to what had previously been observed in tissue culture. To quantify levels of growth promotion, tobacco plants were removed from pots, and the soil was washed away. While washing the soil away it became apparent that although shoot growth was only slightly enhanced in *C. sp* Accession No. NRRL 67603 treated tobacco plants compared to untreated (control) tobacco plants, the root systems of *C. sp* Accession No. NRRL 67603 treated tobacco plants were substantially more extensive than the negative control tobacco plants' root systems. Treated and negative control tobacco plants were subsequently dried in a forced air flow oven and dry weights of whole plant, stems, and roots were measured. Stem tissues are devoid of all leaves and roots. Whole plant and stems of *C. sp* Accession No. NRRL 67603 treated tobacco plants displayed approximately 30% to approximately 40% increases in biomass over untreated control tobacco plants while the roots of *C. sp* Accession No. NRRL 67603 treated tobacco plants showed approximately 290% increase in dry weight over untreated tobacco plants (FIG. 10).

Example 8: Comparison of Growth Stimulation Between *C. sphaerospermum* Accession No. NRRL 67603 and *Trichoderma* Species A handful of publications have shown that *Trichoderma* species produce plant growth stimulants that act either through phytohormones or MVOCs (e.g., Lee, et al., *Fungal Biol Biotechnol* 3:7 (2016)). Some *Trichoderma* species are known to release peptides that are toxic to humans, possibly limiting their potential use in agriculture. An airborne *Trichoderma* isolate of unknown species (attempts to identify the species based on conidiophore and morphological and growth characteristics were unsuccessful) was used to compare its growth promotion effect on tobacco plants derived from preliminary observation with 10-day exposure duration against *C. sp* Accession No. NRRL 67603 MVOCs effect on tobacco plants under identical conditions. For quantitative comparison, the protocol described above using Magenta™ GA7 vessels, 3 cm×4 cm enclosure fungal culture setup, and triplicate treatments along with negative controls were used.

Significantly higher levels of growth stimulation were evident in tobacco plants exposed to *C. sp* Accession No. NRRL 67603 cultures compared to tobacco plants exposed to the *Trichoderma* unknown species. Measurement of various growth characteristics indicated that one month-old tobacco plants treated with 21-day exposure to *C. sp* Accession No. NRRL 67603 had a range of increases from 72% to 297% in some growth characteristics (namely, plant height, plant weight, stem length and leaf length) compared to one month-old tobacco plants treated with the unknown species of *Trichoderma* whereas the number of leaves and root length were approximately similar in both treated tobacco plants (FIG. 11).

Example 9: Comparison of Growth Stimulation Amongst Various *Cladosporium* Species/Isolates At least one other species of *Cladosporium* has been described as enhancing growth of plants via MVOCs. See, e.g., Paul and Park (2013) regarding *C. cladosporiode* isolate CL-1. This study was designed to determine if other *Cladosporium* species produce VOCs that can stimulate plant growth and to compare their effects on tobacco plants.

The protocol described above involving the use of Magenta™ GA7 vessels, 3 cm×4 cm closures, and culture conditions was employed. A total of seven species or isolates were tested for their ability to promote in vitro tobacco growth. Tobacco seeds were germinated as described above. *Cladosporium* were cultured in tube closures as described above. At 6 days after germination, caps containing a single fungus was added to the tobacco plant culture contained in Magenta™ GA7 vessel. The plants were exposed to *Cladosporium* MVOCs for a time period of approximately 15 days or approximately 2 weeks.

Visual differences in plant growth were readily discernable. At that time period, the order of growth stimulation from strongest to weakest ranged from *C. sphaerospermum* Accession No. NRRL 67603>*C. sphaerospermum* NRRL 8131>*C. cladosporioides* 113db>*C. asperulatum* 208db>*C. subtilissimum* WF99-209>*C. cladosporioides* W99-175a>*C. macrocarpum* Clad ex Phyl 8. Among all cultures only plants co-cultured with the *C. sphaerospermum* Accession No. NRRL 67603 reached the top of Magenta™ GA7 vessel and had large-diameter stems and thick leaves.

Noticeably, two isolates of *C. sphaerospermum* showed consistent top-rated stimulation performance (*C. sp* Accession No. NRRL 67603 and *C. sp* Accession No. NRRL 8131). *C. sp* Accession No. NRRL 8131 was previously referenced as *Cladosporium lignicolum* Corda (Dugan, 2008) for its association with sylvan habitat and ability to degrade and absorb nutrients from lignified woody materials. It has never been reported in the literature as being a MVOC producer nor used for promoting plant growth via the MVOC approach. Even though showing plant stimulation at levels relatively similar to *C. sp* Accession No. NRRL 67603, subsequent observations indicated that tobacco plants exposed to MVOCs from *C. sp* Accession No. NRRL 8131 developed large necrotic lesions and, in some cases, the whole plants were scorched with prolonged exposure (>20 days) to this fungal isolate/strain. Such necrotic or phytotoxic response of treated tobacco plants did not occur with *C. sp* Accession No. NRRL 67603 during numerous experiments. In addition, conidiospores of *C. sp* Accession No. NRRL 8131 easily became airborne and contaminated tobacco culture medium in the Magenta™ vessels, thus compromising efforts for growth data collection. It remains unknown whether *C. sp* Accession No. NRRL 8131 is a plant pathogen in nature.

Example 10: Comparison of Growth Stimulation Against Additional *C. sphaerospermum* Isolate To determine if any *C. sphaerospermum* generally produces the increased growth effects as demonstrated above, an additional *C. sphaerospermum* was obtained and tested.

To isolate the target fungus, 100×15 cm Petri plates were filled with 30 ml per plate MS medium (Murashige and Skoog medium supplemented with 3% sucrose and 6 g/L agar) under aseptic condition. Just before use, lids were removed, and culture plates were then placed in kitchen sink areas at a residential home located in Berkeley County, West Virginia for the time duration of 24 hours. Afterwards, they were covered with lids, sealed with parafilm and cultured in a laboratory incubator at 25° C. for 4 days. A single fungal colony with the physical characteristics of *C. sphaerospermum* was identified from one of the test plates based on visual observation of the mycelium with species-specific morphological characteristics, i.e. an olivaceous, powdery, velvety, reverse dark olivaceous-grey appearance along with a hydrophobic hyphal growth pattern as previously described by Dugan et al. (2008). This colony was named MK19 to denote isolation location and year. Subsequently, single conidia were produced through a series of dilution plating on MS medium and used for subsequent examination and testing. MK19 has been deposited at the Agricultural Research Service Culture Collection (NRRL) with an Accession No. 67749.

Microscopic examination was carried out to characterize mycelium, conidiophores and conidia of MK19. Single conidia were grown on MS medium for 7-10 days at 22° C. under continuous light. Transparent adhesive tape (Scotch Magic tape, 3M, St. Paul, Minn., United States) were cut into squares and gently placed along the edge of the colony with forceps. They were then stained for 20 min with 1% aqueous Calcofluor white M2R (Fluorescent brightener 28, Sigma, St. Louis, Mo., United States), gently rinsed in sterile distilled water and mounted between drops of 50% glycerol under a glass cover slip. The cover slip was affixed in place using clear nail polish. Mounted specimens were visualized through confocal microscopy (Zeiss LSM-800, Carl Zeiss AG, Oberkochen, Germany) and images were captured using the manufacturer software.

Results indicate that conidiophores are branched with conidia produced in branching chains with variable shapes and smaller size toward the apex (FIG. 18). Intercalary conidia were 1.81-2.7×3.0-7.7 µm and terminal conidia 1.3-2.1×1.7-3.1 µm. Hyphae was 2.7-3.9 µm wide, sparsely to profusely branched at 45-90° angles, distinctly septate with cell length averaging 20.4 µm and ranging from 15.2 to 24.9 µm. Accordingly, the morphological results were consistent with previously described TC09 (Li et al., *Front. Plant Sci.* 9:1959, 2019) even with minor morphological differences and suggest that MK19 belongs to a new isolate of *C. sp* as described by Dugan et al. (2008) and Ababutain (*Amer. J. App. Sci.* 10:159-163, 2013).

To determine VOC-mediated PGP activity of MK19, surface-sterilized tobacco seeds (*Nicotiana tabacum* cv. Samsun) were germinated on MS medium in Petri dishes. Uniform seedlings were selected and transferred onto Magenta™ GA7 vessels containing MS medium. Fungal cultures were prepared in culture tube closures (Sigma C5791) with conidia solution as previously described (Li et al., 2019) and introduced into tobacco vessels. Experiments were conducted with three replicated plants per vessel and at least two vessels per treatment. Cultures were maintained under light conditions with a 16-hour photoperiod at 25° C. Plant growth was monitored periodically by measuring the vertical length of the largest leaf in each plant. After a 11-day exposure period, plants subjected to fungal VOC exposure from MK19 were significantly larger than control plants without exposure. The former not only displayed robust shoot growth with thicker stem and much larger leaves, but they also produced a more profuse root system than the latter. Minor visual differences in growth pattern were observed between TC09 and MK19. Indeed, incremental measurement of the vertical length of the largest leaf confirmed such subtle, and numerical difference of PGP activity between these two fungal isolates. MK19, the West Virginia strain, was found to be equally effective in stimulating plant growth via VOC as previously demonstrated with tested strains of the same species including strain TC09 with Accession No. NRRL 67603 and strain with Accession No. NRRL 8131 (Li et al., 2019).

Based on these lines of evidence, we conclude that isolates of *C. sphaerospermum*, regardless of their geographic isolation locations or particular strain, possess high levels of VOC-mediated PGP activity.

Example 11: Assessing *C. sphaerospermum* Ability to Stimulate Growth and Yield for Various Plants To determine if *C. sp* Accession No. NRRL 67603 MVOCs positively affect the growth and yield of various plants, switchgrass (*Panicum virgatum*, a monocotyledon), two diploid strawberry species (*Fragaria iinumae* and *F. vesca*; dicotyledon), and cayenne pepper (*Capsicum annuum*; dicotyledon) plants were grown in the presence of *C. sp* Accession No. NRRL 67603 using the above protocols and exposure duration of 20 days.

Switchgrass seedlings grown in vitro and exposed to *C. sp* Accession No. NRRL 67603 had faster growth based on elongation of leaves, stem and roots than untreated switchgrass seedling controls each at 5 days of exposure beginning one day after germination). When the switchgrass was planted to soil after being exposed to the fungus for 20 days, *C. sp* Accession No. NRRL 67603 treated switchgrass plants produced thicker stems, longer/wider leaves and more tillers than negative control switchgrass grown for the same amount of time.

A number of wild species of strawberry are used for genetic and molecular research. However, it is well-known that these species often display growth stagnation during in vitro development, thus causing significant research delays. Up to 9 months are needed to obtain transgenic plants with available strawberry wild species, as such any mechanism to speed up the growth of wild strawberries would benefit the agricultural biotech industry. Two wild strawberry species, *Fragaria iinumae* and *F. vesca* were grown from seeds in vitro for one month and then exposed to *C. sp* Accession No. NRRL 67603 VOCs for 10 days or 20 days and then assessed for an increase in various growth characteristics compared to the same species grown in identical conditions for same number of days but without exposure to *C. sp* Accession No. NRRL 67603 VOCs. Both strawberry species responded positively to the fungus by exhibiting marked growth acceleration at both 10 days and 20 days with increased number of and larger sized leaves, longer and thicker stems, and increased number and length of roots.

It was unknown if *C. sp* Accession No. NRRL 67603 MVOCs accelerate the timing of harvest and/or increase yields in crop plants. Seeking to address this issue, a study was conducted to determine if exposure to *C. sp* Accession No. NRRL 67603 MVOCs would increase a cayenne pepper plant's flowering/fruit set timing and/or yield. *Capsicum annuum* (cayenne pepper cultivar) is in the same family as tobacco (Solanaceae). The cayenne pepper variety used (Long Red Slim) was reported to have an average seed-to-harvest interval of 150-180 days. *C. annuum* (Long Red Slim) seeds were obtained from W. Atlee Burpee & Co. (Item No. 54585A, Warminster, Pa.). Germinated *C. annuum* seeds (6-day-old seedlings from sowing) were exposed to 3 cm×4 cm closure-contained *C. sp* Accession No. NRRL 67603 cultures inside Magenta™ GA7 vessels for 20 days prior to transplant to soil. The above described protocols, including culture vessel setups and light conditions, used for tobacco plants were employed for *C. annuum*. Plant growth and fruit production were monitored continuously until fruit ripening. After in vitro cultivation with 20 days of exposure to *C. sp* Accession No. NRRL 67603 VOCs, *C. sp* Accession No. NRRL 67603 treated pepper plants were significantly larger in shoot and root tissues than negative control pepper plant—similar to what was observed for tobacco. Six negative control pepper plants and six *C. sp* Accession No. NRRL 67603 treated pepper plants were transplanted to soil in 8 inch pots. By 40 days post-germination, *C. sp* Accession No. NRRL 67603 treated pepper plants were not only larger but produced more lateral branches than negative control pepper plants. *C. sp* Accession No. NRRL 67603 treated pepper plants began flowering around 20 days earlier than negative control pepper plants. By 100 days post-germination, negative control pepper plants had reached a similar height as *C. sp* Accession No. NRRL 67603 treated pepper plants, although the negative control pepper plants had relatively fewer lateral branches and fewer flowers. The number of peppers larger than 1 cm in length in negative control pepper plants and treated pepper plants were counted at day 129 and day 136. At these dates, preceding fruit ripening, *C. sp* Accession No. NRRL 67603 treated pepper plants yielded 5-10 times more fruit than negative control pepper plants (FIG. 12). By 145 days, ripening had begun in the *C. sp* Accession No. NRRL 67603 treated pepper plants (10-14 peppers per plant had turned red) but no ripe fruit was observed in the negative control pepper plants. Fruit (cayenne pepper) was harvested at 157 days, and total number of mature fruit plant, total fruit weight per plant, and fruit size were measured. Results showed that *C. sp* Accession No. NRRL 67603 VOCs treatment accelerated vine-ripe pepper harvest by 3 weeks (approximately 26-fold increase) as compared to negative control pepper plants (FIG. 14) and led to an approximately 80% increase in the average total number of vine-ripe fruit per plant and approximately 75% increase in average total fruit weight per plant or yield per plant compared to negative control pepper plants. See FIGS. 13A and 13B. No differences were observed in fruit shape or size from the *C. sp* Accession No. NRRL 67603 VOC exposed pepper plants and the negative control pepper plants (FIG. 15). It should be noted that vine-ripe peppers tend to dehydrate and reduce fresh weight as part of the natural maturation process, hence the yield amount for the *C. sp* Accession No. NRRL 67603 VOC exposed pepper plants may be underrepresented when comparing with all green unripe young peppers from the negative control pepper plants.

Example 12: Using *C. sphaerospermum* to Induce Root Formation for Transplantation and Acclimatization to Soil For multiple decades, large-scale propagation of peach rootstock through tissue culture has been greatly hindered due to recalcitrancy in in vitro shoot proliferation and root induction. As such, growers have been unable to effectively use superior, high-performance clonal peach rootstocks and newly developed varieties in a timely fashion.

A two-step process was tested to induce roots from in vitro shoots and establish plants in the greenhouse. In vitro shoots of the peach rootstock 'Bailey-OP' (*Prunus persica*) of longer than 2 cm in height were first transferred to a modified Lepoivre LP medium (mLP) containing basal salts of LP medium (Quorin and Lepoivre, *Acta Hort.* 78:437-442, 1977) and a vitamin mixture composed of 1.0 mg/L thiamine-HCl, 1.0 mg/L nicotinic acid, 1.0 mg/L pyridoxine-HCl, 4.0 mg/L glycine, 0.2 mg/L biotin and 2.0 mg/L Ca-pathothenate (mLP) supplemented with various concentrations of indole-3-butyric acid (IBA) and cultured for two weeks to induce root primordia. The IBA concentrations ranged from 0.5 to 2.0 mg/L. Shoots with root primordia at the base were then taken out and separated into two groups. The first group was cultured on mLP medium without any growth regulators for continuous plant development as a control, whereas the second group was maintained on a similar growth regulator-free mLP medium but with a culture tube closure containing MVOC-emitting fungus of *C. sp* isolate TC09 (Accession No. NRRL 67603).

Briefly, aqueous conidial suspension was prepared by first culturing the fungal conidia on MS plate for one week followed by collecting conidia in sterile 0.01% Triton X-100/water solution and adjusting density to $1 \times 10^5$ conidia per ml prior to use as inoculum. Aliquots of 5 ml warm MS medium were poured into open-end culture tube closures (Sigma C5791). Once solidified, 10 µl of TC09 suspension, or 1000 conidia in total, was added onto the surface of the medium. One inoculated closure was then placed in each Magenta™ GA7 vessel that contained shoots with induced root primordia for MVOC exposure treatment. Both control and fungal volatile treatment culture vessels were placed under above-mentioned lighting conditions at 25° C. for ten days.

Formation of root primordia from rapidly growing in vitro shoots took place within 10 days after they were placed on mLP containing various concentrations of IBA. Cultivation on 0.5 mg/L IBA resulted a very low root formation efficiency. On the other hand, up to 70%, the highest frequency among all treatments, occurred on mLP supplemented with 1.0 mg/L IBA. Increasing IBA concentration to 1.5 mg/L led to great reduction in root induction efficiency. Further lowered root induction efficiency to less than 20% resulted when 2.0 mg/L IBA was employed.

Although root primordia were induced from in vitro shoots cultured on IBA-containing mLP, these short roots tended to develop significantly enlarged cortical thickness and a large root diameter without lateral roots even during extended cultivation on the same medium beyond the initial 20-day induction cultivation. Earlier attempts to directly transplant over five hundred of these shoots with stubby roots resulted in poor transplant efficiency as few plants could be established in the greenhouse.

In order to mitigate the poor rooting and subsequent acclimatization problems, the use of MVOC emitted by *C. sp* isolate TC09 to stimulate root growth and development and improve plant survival following transplanting was tested. When shoots with root primordia of 1-2 mm in length were transferred onto mLP medium with TC09 MVOC treatment, root growth was altered with substantially enhanced root elongation and normal morphological development. On the other hand, transfer of rooted shoots (shoots having produced root primordia) to similar mLP without TC09 did not show any improvement of root development, but rather excessive callus growth as mentioned above when shoots were cultured on IBA-containing medium (FIG. 16). Roots produced by MVOC-treated shoots grew at a rate of 1-2 cm per day as compared to 0.1-0.2 cm per day in control shoots without MVOC treatment. Consequently, at the end of a 10-day cultivation with TC09, treated shoots (TC09) produced roots measuring 10-15 cm vs a length of 1-1.5 cm in control shoots (Control) during the same cultivation time period (FIG. 16). Secondary lateral roots were also developed in MVOC treated shoots. Roots produced by these shoots had a compact, whitish appearance with slightly enlarged robust root tip. In addition, the size of callus formed at the base was smaller in treated shoots than control shoots. No secondary roots were formed in control shoots during the same cultivation period.

Following transfer to soil in the greenhouse, plantlets previously exposed to TC09 were readily established and started to produce new leaves, whereas control plantlets showed slow growth and signs of transplant shock marked by the death of larger leaves, and many of them died within a short period of time. FIG. 17 depicts the difference in the survival and growth between control (left tray) and MVOC-treated plants (right tray) one month post transplanting. On average, only 37.7% of the transplanted shoots became growing plants from the control group, whereas 86.5% of the transplanted shoots treated with MVOC emitted by TC09 successfully developed into healthy plants. Observations of plant development at early stages revealed that MVOC-treated plants tended to grow relatively faster than control plants without MVOC exposure. Thus far, a large number of 'Bailey-OP' plants have been obtained using the above-described procedure. All plants showed normal bark lignification and formation of lenticels similar to seed-derived plants within a three-month growth duration.

This plant propagation approach showed in vitro multiplication rates increased almost 10 fold as compared to rates of 3-fold of less produced in commercial settings (Battistini and De Paoli, *Acta Hort.* 592:29-33 (2002)). In addition, root primordia were induced from fast-growing in vitro shoots within a short period of time and rooted plants acclimatized to soil conditions at relatively high or doubled efficiencies using MVOC-mediated culture treatment.

Example 13: Assessing *C. sphaerospermum* Ability to Stimulate Growth and Yield for Additional Plants As described above, *C. sp* has been shown to be effective in stimulating growth in switchgrass (*Panicum virgatum*), two diploid strawberry species (*Fragaria iinumae* and *F. vesca*), and cayenne pepper (*Capsicum annuum*) in addition to the other species tested (Tobacco and peach rootstock).

Additional studies were also undertaken with Amaranthaceae (*Amaranthus tricolor*) (FIG. 19), Lamiaceae (Basil, *Ocimum basilicum*) (FIG. 20), Asteraceae (Lettuce, *Lactuca sativa* cv. Grand Rapids) (FIG. 21), Asteraceae (Endive, *Cichorium endivia* var. *latifolia* cv. Broadleaf Batavian) (FIG. 22), Brassicaceae (Kale, *Brassica oleracea* cv. Toscano) (FIG. 23), Brassicaceae (Arugula, *Eruca vesicaria* ssp. *Sativa*) (FIG. 24), and Solanaceae (Tomato, *Solanum lycopersicum* cv. Roma) (FIG. 25). Seed surface sterilization and setup of in vitro plant culture and VOC exposure were carried out using previously described procedure for tobacco and pepper. The images in the above-mentioned figures were taken at the end of a 10- or 20-day exposure treatment time and/or within a specified growth duration following transplanting to soil.

The images from the above experiments clearly demonstrate that *C. sphaerospermum* is useful in stimulating growth and/or yield in a wide variety of plants.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method of increasing at least two growth characteristics of a plant comprising growing a *Cladosporium sphaerospermum* strain in or on a medium in a container, wherein a headspace of said *C. sphaerospermum* in said container is in fluid communication with a headspace of said plant, wherein said *C. sphaerospermum* produces at least one volatile organic compound (VOC), and wherein said at least one VOC produced by said *C. sphaerospermum* causes at least a twofold increase in root biomass, and causes an increase in at least one other growth characteristic, wherein said *C. sphaerospermum* comprises an ITS1/2 consensus amplicon of SEQ ID NO: 5 and an ITS3/4 consensus amplicon of SEQ ID NO: 6.

2. The method of claim 1 wherein said at least one growth characteristic of said plant is selected from the group consisting of growth rate, aerial biomass weight, plant height, number of branches, number of leaves, leaf size, leaf weight, leaf thickness, leaf expansion rate, petiole size, petiole diameter, petiole thickness, stem thickness, branch thickness, trunk thickness stem length, branch length, trunk length, stem weight, branch weight trunk weight, canopy architecture, branching architecture, root extension, root depth, root weight, root diameter, root anchorage, root architecture, abiotic stress tolerance, anthocyanin pigment production, anthocyanin pigment accumulation, plant oil quantity, secondary metabolite accumulation, sensory and flavor compound production, content of phytopharmaceutical compounds, content of phytochemical compounds, fiber hypertrophy, quantity of chlorophyll, photosynthesis rate, photosynthesis efficiency, leaf senescence retardation rate, early fruit set, early fruit maturation, fruit yield, yield of vegetative parts, yield of roots, yield of tubers, yield of fruit, yield of grain, yield of seeds, size of fruit, size of grain, size of seeds, firmness of fruit, weight of fruit, weight of grain, weight of seeds, starch content of vegetative parts, starch content of roots, starch content of tubers, starch content of fruit, starch content of grain, starch content of seeds, sugar content of fruit, sugar content of grain, sugar content of seeds, content of organic acids in fruit and seeds, early flowering, harvest duration, and a combination thereof.

3. The method of claim 1, wherein said plant is a gymnosperm or angiosperm.

4. The method claim 1, wherein said plant is a monocotyledon or dicotyledon.

5. The method of claim 1, wherein growing said *C. sphaerospermum* comprises culturing said *C. sphaerospermum* on at least one of Murashige and Skoog medium, potato dextrose agar, Czapek-DOX Yeast agar, yeast extract agar, malt extract agar, or Hunter's medium.

6. The method of claim 1, wherein said plant is exposed to said at least one VOC for about 1 day.

7. The method of claim 1, wherein said plant is exposed to said at least VOC for between about 1 day and about 30 days.

8. The method of claim 1, wherein said plant is a seedling.

9. The method of claim 1, wherein said *C. sphaerospermum* is at least one of *C. sphaerospermum* Accession No. NRRL 67603, *C. sphaerospermum* Accession No. NRRL 8131, and *C. sphaerospermum* Accession No. NRRL 67749.

\* \* \* \* \*

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: chemically synthesized

<400> SEQUENCE: 1
tccgtaggtg aacctgcgg                                                  19

<210> SEQ ID NO 2
<211> LENGTH: 20
<212> TYPE: DNA
<213> ORGANISM: Artificial Sequence
<220> FEATURE:
<223> OTHER INFORMATION: chemically synthesized

<400> SEQUENCE: 2
gctgcgttct tcatcgatgc                                                 20

<210> SEQ ID NO 3
<211> LENGTH: 20
<212> TYPE: DNA
<213> ORGANISM: Artificial Sequence
<220> FEATURE:
<223> OTHER INFORMATION: chemically synthesized

<400> SEQUENCE: 3
```

```
gcatcgatga agaacgcagc                                              20

<210> SEQ ID NO 4
<211> LENGTH: 22
<212> TYPE: DNA
<213> ORGANISM: Artificial Sequence
<220> FEATURE:
<223> OTHER INFORMATION: chemically synthesized

<400> SEQUENCE: 4
ggaagtaaaa gtcgtaacaa gg                                           22

<210> SEQ ID NO 5
<211> LENGTH: 138
<212> TYPE: DNA
<213> ORGANISM: Cladosporium sphaerospermum

<400> SEQUENCE: 5
ggccggggat gttcataacc ctttgttgtc cgactctgtt gcctccgggg cgaccctgcc   60
ttttcacggg cgggggcccc gggtggacac atcaaaactc ttgcgtaact ttgcagtctg  120
agtaaattta attaataa                                                138

<210> SEQ ID NO 6
<211> LENGTH: 249
<212> TYPE: DNA
<213> ORGANISM: Cladosporium sphaerospermum

<400> SEQUENCE: 6
ttcagtgaat catcgaatct ttgaacgcac attgcgcccc ctggtattcc gggggcatg    60 cctgttcgag cgtcatttca ccactcaagc ctcgcttggt attgggcgac gcggtccgcc  120
gcgcgcctca aatcgaccgg ctgggtcttc tgtcccctca gcgttgtgga aactattcgc  180
taaagggtgc cacgggaggc cacgccgaaa aacaaaccca tttctaaggt tgacctcgga  240
tcaggtagg                                                          249
```